US008551511B2

(12) United States Patent
Brandom et al.

(10) Patent No.: US 8,551,511 B2
(45) Date of Patent: Oct. 8, 2013

(54) PHASE-SEPARATED BIOCOMPATIBLE POLYMER COMPOSITIONS FOR MEDICAL USES

(75) Inventors: Don K. Brandom, La Mesa, CA (US); Durgadas Bolikal, Edison, NJ (US); Lioubov Kabalnova, San Diego, CA (US); James E. McGrath, Blacksburg, VA (US); Joachim Kohn, Piscataway, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 420 days.

(21) Appl. No.: 12/577,203

(22) Filed: Oct. 11, 2009

(65) Prior Publication Data

US 2010/0228343 A1    Sep. 9, 2010

Related U.S. Application Data

(60) Provisional application No. 61/104,724, filed on Oct. 11, 2008, provisional application No. 61/104,728, filed on Oct. 11, 2008.

(51) Int. Cl.
*A61F 13/00* (2006.01)

(52) U.S. Cl.
USPC ...... 424/422; 424/423; 424/78.08; 424/78.17

(58) Field of Classification Search
None
See application file for complete search history.

(56) References Cited

U.S. PATENT DOCUMENTS

| | | |
|---|---|---|
| 3,636,956 A | 1/1972 | Schneider |
| 3,663,515 A | 5/1972 | Hostettler et al. |
| 4,744,365 A | 5/1988 | Kaplan et al. |
| 4,747,956 A | 5/1988 | Kiniwa |
| 4,822,829 A | 4/1989 | Muller et al. |
| 4,980,449 A | 12/1990 | Kohn et al. |
| 5,003,004 A | 3/1991 | Simms |
| 5,066,772 A | 11/1991 | Tang et al. |
| 5,099,060 A | 3/1992 | Kohn et al. |
| 5,216,115 A | 6/1993 | Kohn et al. |
| 5,219,564 A | 6/1993 | Zalipsky et al. |
| 5,403,347 A | 4/1995 | Roby et al. |
| 5,431,679 A | 7/1995 | Bennett et al. |
| 5,587,507 A | 12/1996 | Kohn et al. |
| 5,660,822 A | 8/1997 | Poiani et al. |
| 5,665,831 A | 9/1997 | Neuenschwander et al. |
| 5,670,602 A | 9/1997 | Kohn et al. |
| 5,702,717 A | 12/1997 | Cha et al. |
| 5,854,383 A | 12/1998 | Erneta et al. |
| 5,916,998 A | 6/1999 | Ferruti et al. |
| 5,952,450 A | 9/1999 | Ishihara et al. |
| 6,120,491 A | 9/2000 | Kohn et al. |
| 6,228,969 B1 | 5/2001 | Lee et al. |
| 6,355,754 B1 | 3/2002 | Olson et al. |
| 6,475,477 B1 | 11/2002 | Kohn et al. |
| 6,592,899 B2 | 7/2003 | Fowers et al. |
| 6,602,497 B1 | 8/2003 | Kohn et al. |
| 6,943,214 B2 | 9/2005 | Flexman |
| 7,166,134 B2 | 1/2007 | Datta et al. |
| 7,169,187 B2 | 1/2007 | Datta et al. |
| 7,479,157 B2 | 1/2009 | Weber et al. |
| 2001/0046505 A1 | 11/2001 | Kohn et al. |
| 2003/0068384 A1 | 4/2003 | Brocchini et al. |
| 2004/0082734 A1 | 4/2004 | Hatton et al. |
| 2005/0106119 A1 | 5/2005 | Brandom et al. |
| 2006/0024266 A1 | 2/2006 | Brandom et al. |
| 2006/0034769 A1 | 2/2006 | Kohn et al. |
| 2006/0034891 A1 | 2/2006 | Lawin et al. |
| 2006/0036316 A1 | 2/2006 | Zeltinger et al. |
| 2006/0178477 A1 | 8/2006 | Neuenschwander |
| 2007/0117959 A1 | 5/2007 | Shastri et al. |
| 2007/0231365 A1 | 10/2007 | Wang et al. |
| 2007/0282435 A1 | 12/2007 | Wang et al. |
| 2008/0063685 A1 | 3/2008 | Wang et al. |
| 2008/0112999 A1 | 5/2008 | Baluca |
| 2008/0146504 A1 | 6/2008 | Bonnin |
| 2008/0152690 A1 | 6/2008 | Kohn et al. |
| 2008/0187567 A1 | 8/2008 | Kohn et al. |
| 2008/0243049 A1 | 10/2008 | Hardy |
| 2008/0243228 A1 | 10/2008 | Wang et al. |
| 2008/0269874 A1 | 10/2008 | Wang et al. |
| 2009/0004243 A1 | 1/2009 | Pacetti et al. |
| 2009/0035350 A1 | 2/2009 | Stankus et al. |
| 2009/0088835 A1 | 4/2009 | Wang |

FOREIGN PATENT DOCUMENTS

WO    9836013 A1    8/1998

OTHER PUBLICATIONS

Teng et al., "Synthesis and characterization of poly(L-lactic acid)-poly(ε-caprolactone) multiblock copolymers by melt polycondensation," Journal of Polymer Science Part A: Polymer Chemistry. 42: pp. 5045-5053, 2004. (Abstract).
Dobrzynski et al. Structure-Property Relationships of Copolymers Obtained by Ring-Opening Polymerization of Glycolide and ε-Caprolactone. Part 1. Synthesis and Characterization. Biomacromolecules 6(1): 483-488. 2005.
International Search Report and Written Opinion issued on Dec. 3, 2009 for International Application No. PCT/US09/60301.
Sousa, A., et al., "Selective Protein Adsorption on a Phase-Separated Solvent-Cast Polymer Blend", Langmuir, 22, 2006, pp. 6286-6292.
Tangpasuthadol, V., et al., "Thermal properties and physical ageing behaviour of tyrosine-derived polycarbonates", Biomaterials, 1996, vol. 17, No. 4., pp. 463-468.
Sakar, D., et al., Structure-Property Relationship of L-Tyrosine-Based Polyurethanes for Biomaterial Applications, Journal of Applied Polymer Science, vol. 108, 23435-2355 (2008).
Polycarprolactone diol, 2011 obtained from the Sigma-Aldrich website: (http://www.sigmaaldrich.com/catalog/ProductDetail.do?D7=0&N5=SEARCH_CONCAT_PNO%7CBRAND_KEY&N4=189421%7CALDRICH&N25=0&QS=ON&F=SPEC).

(Continued)

*Primary Examiner* — James Rogers
(74) *Attorney, Agent, or Firm* — Fox Rothschild LLP

(57) ABSTRACT

A variety of phase-separated biocompatible polymer compositions are described. In preferred embodiments the polymers are bioresorbable and/or biodegradable, and have desirable mechanical properties, such as fracture and/or fatigue toughness, that have previously not been a primary design criteria for such polymers. The polymer compositions are useful in a variety of medical applications, such as in the fabrication of medical devices.

61 Claims, 1 Drawing Sheet

(56) References Cited

OTHER PUBLICATIONS

Nathan et al., Bio. Cong. Chem., 4, 54-62 (1993).
Nathan, Macromol., 25, 4476 (1992).
Dobrzynski et al. Structure-Property Relationships of Copolymers Obtained by Ring-Opening Polymerization of Glycolide and e-Caprolactone. Part 1. Synthesis and Characterization. Biomacromolecules 6(1): 483-488. 2005.
Teng et al., "Synthesis and characterization of poly(L-lactic acid)-poly(e-caprolactone) multiblock copolymers by melt polycondensation," Journal of Polymer Science Part A: Polymer Chemistry. 42: pp. 5045-5053, 2004. (Abstract).
Mligiliche et al., ",Poly lactic acid-caprolactone copolymer tube with a denatured skeletal muscle segment inside as a guide for peripheral nerve regeneration: A morphological and electrophysiological evaluation of the regenerated nerves," Anatomical Science International, vol. 78, No. 3, Sep. 2003, pp. 156-161. (Abstract).

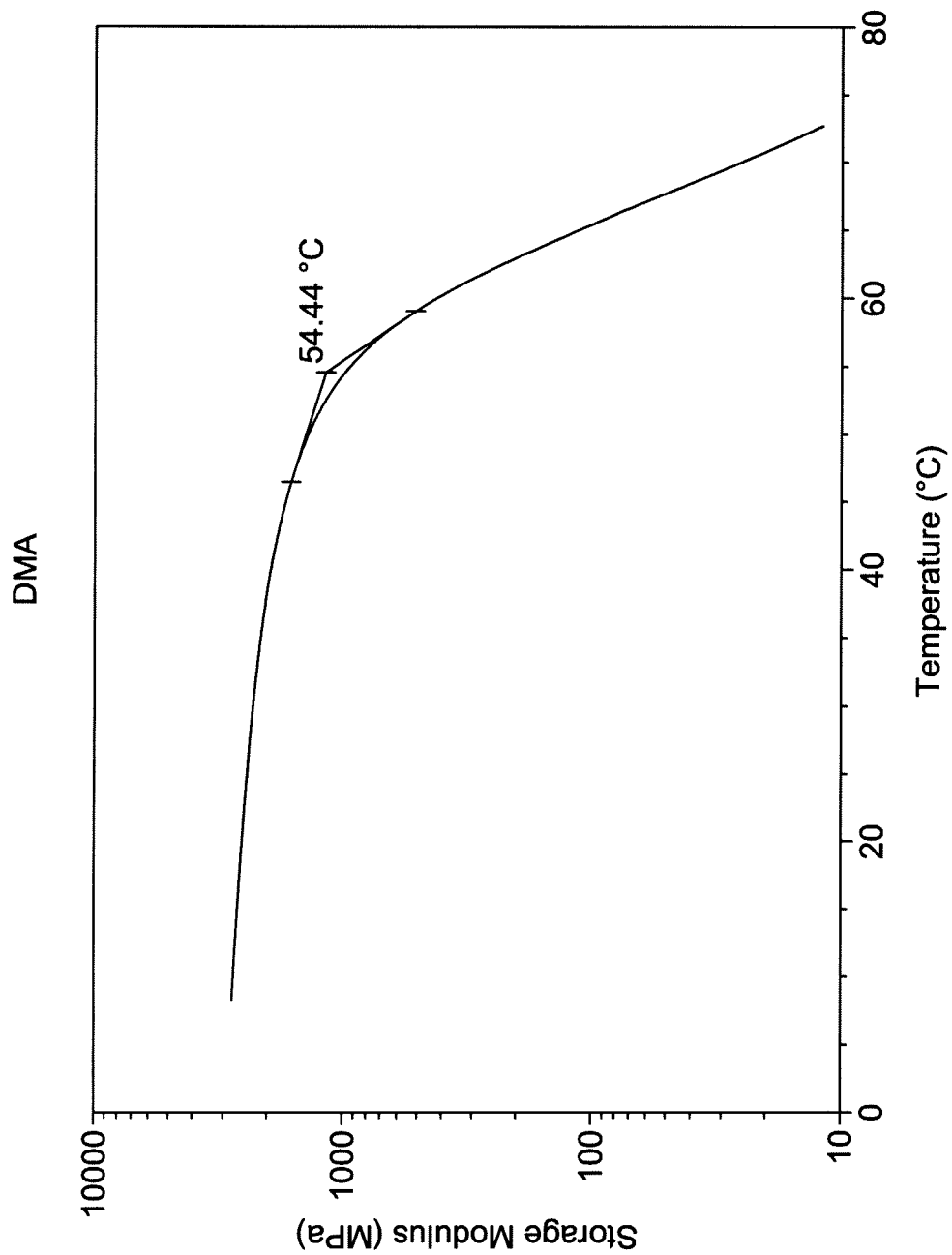

PHASE-SEPARATED BIOCOMPATIBLE POLYMER COMPOSITIONS FOR MEDICAL USES

CROSS-REFERENCE TO RELATED APPLICATIONS

This application claims priority under 35 U.S.C. §119(e) to U.S. Provisional Patent Application Ser. Nos. 61/104,724 and 61/104,728, both of which were filed Oct. 11, 2008, and both of which are hereby incorporated by reference in their entirety for all purposes.

This application is also related to a U.S. patent application entitled "Biocompatible Polymers for Medical Devices" and U.S. Provisional Patent Application Ser. Nos. 61/250,545, 61/250,548 and 61/250,550, all of which were filed on the same date of the present application. The disclosures of all three applications are hereby incorporated by reference in their entirety for all purposes.

BACKGROUND OF THE INVENTION

1. Field of the Invention

The present invention relates to new classes of biocompatible polymers, including novel biodegradable and/or bioresorbable polymers. These polymers, while not limited thereto, may be adapted for radio-opacity and are useful for medical device applications and controlled release therapeutic formulations.

2. Description of the Related Art

The rapidly evolving field of bioengineering has created a demand for a diverse library of different types of polymers offering a wide variety of choice of physical and mechanical properties. It is desirable that libraries of many different materials be available so that the specific polymer properties can be optimally matched with the requirements of the specific applications under development.

Examples of polymers suitable for various bioengineering applications include those described in U.S. Pat. Nos. 5,099,060; 5,665,831; 5,916,998 and 6,475,477, along with the polymers described in U.S. Patent Publication Nos. 2006/0024266 and 2006/0034769. There are numerous applications in which it is considered desirable for an implanted medical device to maintain its integrity and performance characteristics for extended periods of time, even under demanding mechanical conditions such as repeated mechanical flexure. Although many types of bioresorbable and/or biodegradable polymers are known, they are generally not selected for such applications because they were designed for temporary presence in the body and therefore lacked the desired combination of physical and mechanical properties. In addition, bioresorbtion and/or biodegradation tend to alter mechanical properties in unpredictable ways that are not necessarily linearly related to each other. Thus, there is a need for biocompatible, bioresorbable and/or biodegradable polymers having desirable mechanical properties, such as fracture and/or fatigue toughness, that have previously not been a primary design criteria for such polymers.

SUMMARY OF THE INVENTION

Various embodiments provide phase-separated polymer compositions, medical devices containing such compositions, and methods of using such polymer compositions and devices.

An embodiment provides a biocompatible polymer composition, comprising at least a first polymer phase and a second polymer phase;

the first polymer phase having at least one first wet thermal transition temperature selected from a first wet glass transition temperature and a first wet melting point, the first wet thermal transition temperature being at least 38° C.;

the first polymer phase comprising a number (n) of first recurring units of frmula (I):

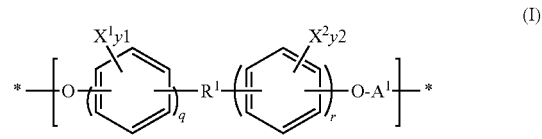

wherein:

$X^1$ and $X^2$ are each independently selected from the group consisting of halogen, halomethyl, halomethoxy, methyl, methoxy, thiomethyl, nitro, sulfoxide, and sulfonyl;

$y^1$ and $y^2$ indicate the number of $X^1$ and $X^2$ groups, respectively, and are each independently zero or an integer in the range of 1 to 4;

q and r are each independently zero or one, where q+r=1 or 2;

each $A^1$ is independently selected from the group consisting of

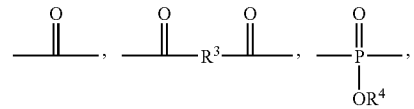

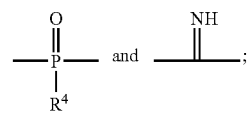

each $R^3$ is independently selected from the group consisting of $C_1$-$C_{30}$ alkyl, $C_1$-$C_{30}$ heteroalkyl, $C_5$-$C_{30}$ aryl, $C_6$-$C_{30}$ alkylaryl, and $C_2$-$C_{30}$ heteroaryl;

each $R^4$ independently selected from the group consisting of H, $C_1$-$C_{30}$ alkyl, and $C_1$-$C_{30}$ heteroalkyl;

each $R^1$ is independently selected from the group consisting of

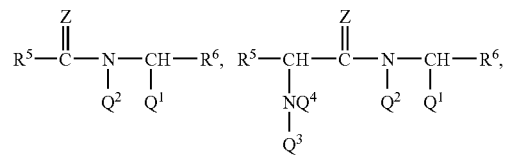

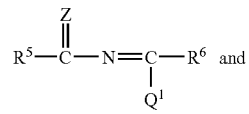

-continued

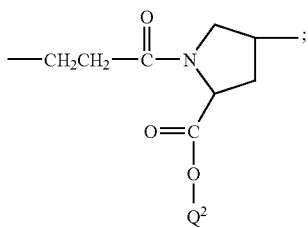

provided that when R¹ is

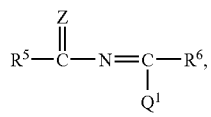

Q₁ is COOR₄ and when R¹ is

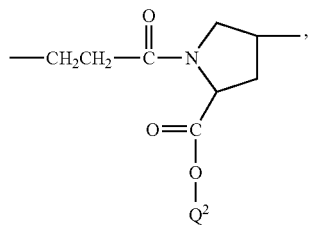

r=0;
R⁵ is selected from the group consisting of —CH═CH—, —CHJ¹-CHJ²-, —(CH₂)ₐ—, optionally ring-halogenated

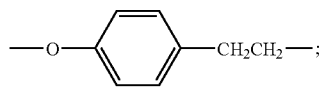

and optionally ring-halogenated

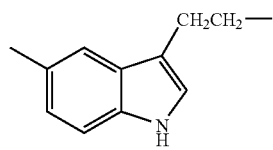

in which case q=0;
R⁶ is selected from the group consisting of —CH═CH—, —CHJ¹-CHJ²-, —(CH₂)ₐ—, optionally ring-halogenated

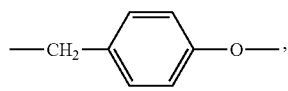

and optionally ring-halogenated

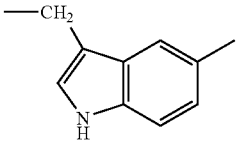

in which case r=0;
each a is independently zero or an integer in the range of 1 to 8;
J¹ and J² are each independently selected from the group consisting of Br and I;
each Z is independently an O or an S; and
Q¹ and Q⁴ are each independently H, CH₂—R⁴, COOR⁴ or a crystallizable group comprising from about 6 to about 30 carbon atoms;
Q² and Q³ are each independently H, CH₂—R⁴, or a crystallizable group comprising from about 6 to about 30 carbon atoms;
the second polymer phase having at least one second wet thermal transition temperature selected from a second wet glass transition temperature and a second wet melting point, the second wet thermal transition temperature being 36° C. or lower, the second polymer phase comprising a number (m) of second recurring units;
wherein the number (n) and the number (m) are selected to control the relative amounts of the first polymer phase and the second polymer phase so that (a) the polymer composition is phase-separated over at least the temperature range of about 25° C. to about 50° C., (b) the polymer composition has a water content of 4.5% or less as measured after soaking for 24 hours at 37° C. in 0.1 M phosphate buffered saline (PBS) at pH 7.4; and (c) the volume fraction of the second polymer phase in the polymer composition is in the range of about 6% to about 40%, based on total volume.

Another embodiment provides a polymer composition as described above, wherein the second recurring units have a formula selected from the group consisting of the formula (IIa), the formula (IIb), the formula (IIc), and the formula (IId):

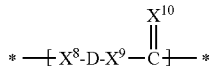 (IIa)

 (IIb)

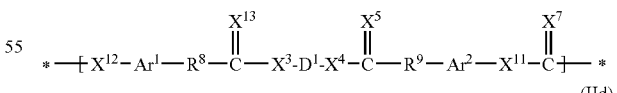 (IIc)

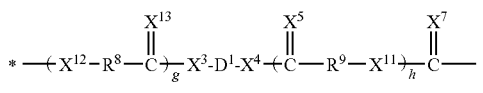 (IId)

wherein X³, X⁴, X⁵, X⁷, X⁸, X⁹, X¹⁰, X¹¹, X¹² and X¹³ are independently selected from the group consisting of O, S and NR¹⁰, where R¹⁰ is selected from hydrogen and an alkyl group containing from one to 30 carbon atoms;
Ar¹ and Ar² are phenyl rings optionally substituted with from one to four substituents independently selected from the group consisting of a halogen, a halomethyl, a halomethoxy, a methyl, a methoxy, a thiomethyl, a nitro, a sulfoxide, and a sulfonyl;

$R^8$ and $R^9$ contain from one to ten carbon atoms each and are independently selected from the group consisting of an optionally substituted alkylene, an optionally substituted heteroalkylene, an optionally substituted alkenylene, and an optionally substituted heteroalkenylene;

g and h in formula (IId) are each independently integers in the range of about 1 to about 500; and D and $D^1$ contain up to 24 carbon atoms and are independently selected from the group consisting of an optionally substituted alkylene, an optionally substituted heteroalkylene, an optionally substituted alkenylene and an optionally substituted heteroalkenylene;

or D, $X^8$ and $X^9$ in formula (IIa) are selected so that $HX^8$-D-$X^9$H defines a hydroxyl endcapped macromer, a mercapto endcapped macromer or an amino endcapped macromer;

or $D^1$, $X^3$ and $X^4$ in formula (IIc) are selected so that $HX^3$-$D^1$-$X^4$H defines a hydroxyl endcapped macromer, a mercapto endcapped macromer or an amino endcapped macromer.

Another embodiment provides a medical device that comprises a polymer and/or polymer composition as described herein. For example, an embodiment provides a stent that comprises a polymer composition as described herein. Another embodiment provides a method of treating a body lumen, comprising deploying the stent within the body lumen.

These and other embodiments are described in greater detail below.

BRIEF DESCRIPTION OF THE DRAWINGS

FIG. 1 illustrates the determination of the wet glass transition temperature (Tg) of a polymer by dynamic mechanical analysis (DMA). The Tg is indicated by the intersection of the respective tangent lines before and after the onset of drop in storage modulus E'.

DETAILED DESCRIPTION OF THE PREFERRED EMBODIMENTS

The present invention relates to new classes of phase-separated polymeric materials which, while not limited thereto, are fracture- and/or fatigue-toughened, may be adapted for radio-opacity and are useful for medical device applications and controlled release therapeutic formulations, although not limited thereto.

Abbreviations and Nomenclature

As used herein, the terms "macromer", "macromeric" and similar terms have the usual meaning known to those skilled in the art and thus may be used to refer to oligomeric and polymeric materials that are functionalized with end groups that are selected so that the macromers can be copolymerized with other monomers. A wide variety of macromers and methods for making them are known to those skilled in the art. Examples of suitable macromers include hydroxy endcapped polylactic acid macromers, hydroxy endcapped polyglycolic acid macromers, hydroxy endcapped poly(lactic acid-co-glycolic acid) macromers, hydroxy endcapped polycaprolactone macromers, poly(alkylene diol) macromers, hydroxy endcapped poly(alkylene oxide) macromers and hydroxy endcapped polydioxanone macromers.

As used herein, the terms "tough", "toughened", "toughness" and similar terms have the usual meaning known to those skilled in the art and thus may be used to refer to the resistance of a polymer under a static or dynamic load (or strain) to brittle failure from crack propagation within a glassy or semicrystalline phase. Examples of toughened polymers include fracture-toughened polymers and fatigue-toughened polymers. Preferred toughened polymer compositions contain multiple phases, including a toughening phase (such as an elastomeric phase) that is present in an amount that is effective to toughen the polymer composition, as compared to an otherwise comparable polymer composition lacking the toughening phase. The toughening phase may be a discrete phase that is not covalently attached to the other phase(s), or the polymer composition may include a block copolymer that phase separates in such a way as to form a toughening phase.

As used herein, the terms "polymer", "polymeric" and similar terms have the usual meaning known to those skilled in the art and thus may be used to refer to homopolymers, copolymers (e.g., random copolymer, alternating copolymer, block copolymer, graft copolymer) and mixtures thereof.

As used herein, the term "molecular weight" has the usual meaning known to those skilled in the art and thus reference herein to a polymer having a particular molecular weight will be understood as a reference to a polymer molecular weight in units of Daltons. Various techniques known to those skilled in the art, such as end group analysis (e.g., by $^1$H NMR) and high pressure size exclusion chromatography (also known as gel permeation chromatography, "GPC"), may be used to determine polymer molecular weights. In some cases the molecular weights of polymers are further described herein using the terms "number average" molecular weight (Mn) and/or "weight average" molecular weight (Mw), both of which terms are likewise expressed in units of Daltons and have the usual meaning known to those skilled in the art. In the event of that the value for the molecular weight of a polymer as determined by a particular technique conflicts with the value obtained by a different technique, the following procedure is used to resolve the conflict. An attempt is made to measure the number average molecular weight of the polymer by end group analysis using $^1$H NMR. If $^1$H NMR indicates that the number average molecular weight is greater than 10,000, then the molecular weight of the polymer is determined by GPC using low angle laser light scattering (LALLS) detection. On the other hand, if $^1$H NMR indicates that the number average molecular weight is 10,000 or less, then the molecular weight of the polymer is determined by end group analysis using $^1$H NMR.

As used herein, the terms "phase separated," "phase separation" and similar terms have the usual meaning known to those skilled in the art and thus may be used to refer to polymeric materials that contain multiple phases, e.g., a polymeric material that contains a glassy phase and an elastomeric phase, a polymeric material that contains a crystalline phase and an elastomeric phase, a polymeric material that contains a semi-crystalline phase and an elastomeric phase, a polymeric material that contains a glassy phase, a semi-crystalline phase and an elastomeric phase, etc. The presence of phase separation may determined by one or more of a number of accepted methodologies, e.g., small angle neutron scattering (SANS), small angle x-ray scattering (SAXS), transmission electron microscopy (TEM), atomic force microscopy (AFM), and/or by the detection of multiple phase transitions attributable to each of the phases by differential scanning calorimetry (DSC), dynamic mechanical analysis (DMA), dielectric analysis (DEA), and/or thermal mechanical analysis (TMA). In the event that the results obtained by any two or more techniques conflict with one another, phase separation is to be determined by SAXS. Those skilled in the art will appreciate that phase separation can occur on various scales, e.g., microphase separation, nanophase separation, etc., and that phase separation may occur between two different polymers or between two phases of the same polymer. For example, some embodiments are directed to phase-separated block copolymers. In some embodiments a polymer composition is said to be phase-separated over a particular temperature range, e.g., over at least the temperature range of about 25° C. to about 50° C. This means that the polymer composition remains phase separated over the indicated range of temperatures. Phase separation over the entire range may be determined by confirming phase separation at three representative temperatures within the range, e.g., at the upper end of the range (e.g., about 50° C.), at the lower end of the range (e.g., about 25° C.) and in the middle of the range (e.g., about 37° C.).

The term "volume fraction" has the usual meaning known to those skilled in the art and thus may be used to refer to the respective amounts of two or more polymer components within a polymer composition, e.g., two or more phases. In many cases volume fraction is difficult to determine experimentally and thus for the purposes of this patent application the volume fraction is a calculated value based on the respective densities and masses of the individual polymer components. The calculation is not adjusted for phase mixing (if any) and is not adjusted for differences in density (if any) between amorphous and crystalline regions within a particular material. For example, for a three-component polymer composition, the total volume of the polymer composition, $V_P$, is defined as the sum of the volumes of the three components in the polymer composition, $V_1+V_2+V_3$, as follows:

$$V_P = V_1 + V_2 + V_3$$

The volumes of the three components are defined in terms of their individual masses and densities, as follows:

$V_1 = M_1/D_1$, where $M_1$ and $D_1$ are the mass and density of component 1, respectively.

$V_2 = M_2/D_2$, where $M_2$ and $D_2$ are the mass and density of component 2, respectively.

$V_3 = M_3/D_3$, where $M_3$ and $D_3$ are the mass and density of component 3, respectively.

The volume fraction of each component is thus calculated as the volume of that component divided by the total volume:

Volume fraction of first component=$V_1/V_P$.
Volume fraction of second component=$V_2/V_P$.
Volume fraction of second component=$V_3/V_P$.

The masses (e.g., $M_1$, $M_2$ and $M_3$) are determined from knowledge of the formulation for the particular polymer composition being made, and the densities (e.g., $D_1$, $D_2$ and $D_3$) are based on the densities of each of the individual component, as measured in isolation. An example calculation is provided in Table 1 below for an $I_2$DTE-PCL10k-PCL1.25k polymer composition made by using phosgene to copolymerize $I_2$DTE monomer ("$I_2$DTE") with hydroxy-endcapped PCL macromer having a molecular weight of about 10,000 ("PCL10k") and hydroxy-endcapped PCL macromer having a molecular weight of about 1250 ("PCL1.25k").

TABLE 1

| Component | Mass in composition (normalized to a 1 g batch (g)) | Measured Density (g/cc) | Calculated Volume (cc) | Calculated Volume fraction (×100%) |
|---|---|---|---|---|
| $I_2$DTE | 0.85 | 1.78 g/cc | 0.478 | 79% |
| PCL10k | 0.080 | 1.17 g/cc | 0.069 | 11% |
| PCL1.25k | 0.070 | 1.17 g/cc | 0.060 | 10% |

The volume fraction of the various phases in a phase-separated composition is determined similarly. For the purposes of the volume fraction calculation, a component of the formula (I) is considered to be phase-separated from a component that is not of the formula (I) if the component that is not of the formula (I) has a molecular weight of greater than 5,000. If two components of the formula (I) have essentially the same chemical composition but different molecular weights, then both are considered to be in the same (first) phase. If two components that are not of the formula (I) (e.g., two components of the formula (II)) have essentially the same chemical composition but different molecular weights, they are both considered to be in the same (second) phase if both of their molecular weights are greater than 5,000. However, if a component is not of the formula (I) and has a molecular weight of 5,000 or less, it is considered to be in the first phase. For example, the $I_2$DTE-PCL10k-PCL1.25k polymer composition illustrated in Table 1 is considered to be phase-separated over the temperature range of 25° C. to 50° C. into two phases, an $I_2$DTE (first) phase and a PCL (second) phase. The $I_2$DTE component is considered to be phase separated from the PCL10k component because the PCL10k component has a molecular weight that is greater than 5,000. The PCL1.25k component has a molecular weight that is less than 5,000 and thus is considered to be in the same phase as the $I_2$DTE component. Thus, the volume fraction of the $I_2$DTE phase in the $I_2$DTE-PCL10k-PCL1.25k polymer composition illustrated in Table 1 is considered to be 89% (sum of calculated volume fractions of $I_2$DTE and PCL1.25k), and the volume fraction of the PCL phase is considered to be 11% (calculated volume fraction of PCL-10k).

The term "thermal transition temperature" has the usual meaning known to those skilled in the art and thus may be used to refer to both first order thermal transitions and second order thermal transitions. The first order thermal transition of a polymer or phase thereof may be referred to herein as a "melting point" or "Tm", and the second order thermal transition of a polymer or phase thereof may be referred to herein as a "glass transition temperature" or "Tg". Those skilled in the art will appreciate that a polymeric material or phase thereof may have exhibit either or both types of thermal transitions, as well as higher order thermal transitions. Thermal transition temperature may be determined by methods known to those skilled in the art, such as by DSC, DMA, DEA and TMA. In some cases the presence of a particular phase within a polymer composition may be detectable by a technique such as SAXS, but the amount of that phase in the polymer composition may be relatively small, such that measurements of the thermal transition temperature(s) for that phase may be difficult or imprecise. In such instances, the thermal transitions temperatures may be determined by applying the measurement technique (e.g., DSC, DMA, DEA and/or TMA) to a bulk sample of a polymer composed of the recurring units present in that phase.

The term "wet" thermal transition temperature, e.g., "wet" melting point and "wet" glass transition temperature, refers to a thermal transition temperature of a polymer or phase thereof that is determined using a sample of the polymer that has been pre-conditioned to be in a wet state during the measurement by soaking the polymer for 24 hours at 37° C. in 0.1 M phosphate buffered saline (PBS) at pH 7.4. Wet thermal transition temperatures may be measured using various techniques known to those skilled in the art. In the event that the results obtained by any two or more techniques conflict with one another, DMA is used to determine wet thermal transition temperatures. DMA monitors changes in the viscoelastic properties (storage modulus, loss modulus, and tan delta) of a material as a function of temperature under oscillating deformation (stress or strain). The terms "stress at yield (σ)," "modulus (E)", and "elongation at break (s)" have the usual meanings known to those skilled in the art. Although in principle all three viscoelastic properties can be used to define the Tg, for the present purposes Tg and/or Tm are determined by measuring the onset of drop in storage modulus E', as indicated by the intersection of the respective tangent lines before and after the transition. See FIG. 1. Wet Tg and/or Tm can be determined using DMA by employing a submersion clamp apparatus that allows a film strip sample to be tested within a liquid environment. A thin (0.1 mm) strip of thermo-pressed polymer film is submerged in water and subjected to a multi-frequency-strain mode and heated at a constant rate. While heating, the material is deformed (oscillated) at constant amplitude (strain) over a range of frequencies (or single frequency) and mechanical properties measured, using the following DMA instrument parameters: temperature ramp: heat at rate of 2° C./min over temperature range of 5° C. to 80° C.; oscillating amplitude 20 μm; pre-load=0.01 N; frequency=1.2 Hz.

Because the sample is wet, the appearance of the E' onset parameter can only be determined within the range of about 5° C. to about 80° C. because of the physical limitations due to the freezing and vaporization of water. If a wet transition is not found within the 5° C. to 80° C. range, then another analysis is performed in the dry state over a much greater temperature range, e.g., −150° C. to 200° C., and a new Tg analysis is made. With the dry Tg information, in combination with the lack of a wet transition, the wet Tg is thereby determined to be either below 5° C. or above 80° C., as the case may be.

The terms "radiopaque", "radio-opaque", "radiopacity", "radio-opacity", "radiopacifying" and similar terms have the usual meaning known to those skilled in the art and thus may be used to refer to polymer compositions that have been rendered easier to detect using medical imaging techniques (e.g., by X-ray and/or during fluoroscopy) being the incorporation of heavy atoms into the polymer composition. Such incorporation may be by mixing, e.g., by mixing an effective amount of a radiopacifying additive such as barium salt or complex, and/or by attachment of effective amounts of heavy atoms to one or more of the polymers in the polymer composition. For example, attachment of heavy atoms to a polymer in sufficient amounts may advantageously render the polymer easier to detect by various medical imaging techniques. The term "heavy atom" is used herein to refer to atoms having an atomic number of 17 or greater. Preferred heavy atoms have an atomic number of 35 or greater, and include bromine, iodine, bismuth, gold, platinum tantalum, tungsten, and barium. In certain configurations, polymer compositions may be inherently radiopaque. The term "inherently radiopaque" is used herein to refer to a polymer to which a sufficient number of heavy atoms are attached by covalent or ionic bonds to render the polymer radiopaque. This meaning is consistent with the understanding of those skilled in the art, see, e.g., U.S. Patent Publication No. 2006/0024266, which is hereby incorporated by reference for all purposes, including for the particular purpose of describing radiopaque polymeric materials.

The terms "alkyl", "alkylene" and similar terms have the usual meaning known to those skilled in the art and thus may be used to refer to straight or branched hydrocarbon chain fully saturated (no double or triple bonds) hydrocarbon group. Terminal alkyl groups, e.g., of the general formula —$C_nH_{2n+1}$, may be referred to herein as "alkyl" groups, whereas linking alkyl groups, e.g., of the general formula —$(CH_2)_n$—, may be referred to herein as "alkylene" groups. The alkyl group may have 1 to 50 carbon atoms (whenever it appears herein, a numerical range such as "1 to 50" refers to each integer in the given range; e.g., "1 to 50 carbon atoms" means that the alkyl group may consist of 1 carbon atom, 2 carbon atoms, 3 carbon atoms, etc., up to and including 50 carbon atoms, although the present definition also covers the occurrence of the term "alkyl" where no numerical range is designated). The alkyl group may also be a medium size alkyl having 1 to 30 carbon atoms. The alkyl group could also be a lower alkyl having 1 to 5 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl and the like.

The alkyl group may be substituted or unsubstituted. When substituted, the substituent group(s) is(are) one or more group(s) individually and independently selected from alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, ester, mercapto, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalo-methanesulfonamido, and amino, including mono- and di-substituted amino groups, and the protected derivatives thereof.

The terms "alkenyl", "alkenylene" and similar terms have the usual meaning known to those skilled in the art and thus may be used to refer to an alkyl or alkylene group that contains in the straight or branched hydrocarbon chain one or more double bonds. An alkenyl group may be unsubstituted or substituted. When substituted, the substituent(s) may be selected from the same groups disclosed above with regard to alkyl group substitution unless otherwise indicated.

The terms "heteroalkyl", "heteroalkylene," and similar terms have the usual meaning known to those skilled in the art and thus may be used to refer to an alkyl group or alkylene group as described herein in which one or more of the carbons atoms in the backbone of alkyl group or alkylene group has been replaced by a heteroatom such as nitrogen, sulfur and/or oxygen. Likewise, the term "heteroalkenylene" may be used to refer to an alkenyl or alkenylene group in which one or more of the carbons atoms in the backbone of alkyl group or alkylene group has been replaced by a heteroatom such as nitrogen, sulfur and/or oxygen.

The term "aryl" has the usual meaning known to those skilled in the art and thus may be used to refer to a carbocyclic (all carbon) monocyclic or multicyclic aromatic ring system that has a fully delocalized pi-electron system. Examples of aryl groups include, but are not limited to, benzene, naphthalene and azulene. The ring of the aryl group may have 5 to 50 carbon atoms. The aryl group may be substituted or unsubstituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxy, alkoxy, aryloxy, acyl, ester, mercapto, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof, unless the substituent groups are otherwise indicated. An aryl group substituted with alkyl may be referred to herein as "alkylaryl."

The term "heteroaryl" has the usual meaning known to those skilled in the art and thus may be used to refer to a monocyclic or multicyclic aromatic ring system (a ring system with fully delocalized pi-electron system) that contain(s) one or more heteroatoms, that is, an element other than carbon, including but not limited to, nitrogen, oxygen and sulfur. The ring of the heteroaryl group may have 5 to 50 atoms. The heteroaryl group may be substituted or unsubstituted. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxy, alkoxy, aryloxy, acyl, ester, mercapto, cyano, halogen, carbonyl, thiocarbonyl, O-carbamyl, N-carbamyl, O-thiocarbamyl, N-thiocarbamyl, C-amido, N-amido, S-sulfonamido, N-sulfon-amido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalo-methanesulfonamido, and amino, including mono- and di-substituted amino groups, and the protected derivatives thereof.

The term "crystallizable" has the usual meaning known to those skilled in the art, see U.S. Patent Publication No. 20060024266, which is incorporated herein by reference for all purposes and particularly for the purpose of describing crystallizable groups. Polymers that contain crystallizable groups that are attached to the sides of the polymer, known as side chain crystallizable (SCC) polymers or "comb-like" polymers, are well-known, see N. A. Plate and V. P. Shibaev, J. Polymer Sci.: Macromol. Rev. 8:117-253 (1974), the disclosure of which is hereby incorporated by reference. In an embodiment, a polymer as described herein contains crystallizable side groups and thus may be regarded as a SCC polymer. It will be understood that the crystallizable side chains of SCC polymers are preferably selected to crystallize with one another to form crystalline regions and may comprise, for example, $—(CH_2)_x—$ and/or $—((CH_2)_y—O—)_x$ groups. The side chains are preferably linear to facilitate crystallization. For SCC polymers that contain $—(CH_2)_x—$ groups in the crystallizable side chain, x is preferably in the range of about 6 to about 30, more preferably in the range of about 20 to about 30. For SCC polymers that contain $—((CH_2)_y—O—)_x$ groups in the crystallizable side chain, x is preferably in the range of about 6 to about 30 and y is preferably in the range of about 1 to about 8. More preferably, x and y are selected so that the $((CH_2)_y—O—)_x$ groups contain from about 6 to about 30 carbon atoms, even more preferably from about 20 to about 30 carbon atoms. The spacing between side chains and the length and type of side chain are preferably selected to provide the resulting SCC polymer with a desired melting point. As the spacing between side chains increases, the tendency for the side chains to be crystallizable tends to decrease Likewise, as the flexibility of the side chains increases, the tendency for the side chains to be crystallizable tends to decrease. On the other hand, as the length of the side chains increases, the tendency for the side chains to be crystallizable tends to increase. In many cases, the length of the crystallizable side chain may be in the range of about two times to about ten times the average distance between crystallizable side chains of the SCC polymer.

Whenever a group is described as being "optionally substituted" that group may be unsubstituted or substituted with one or more of the indicated substituents. Likewise, when a group is described as being "unsubstituted or substituted" if substituted, the substituent may be selected from one or more the indicated substituents.

Unless otherwise indicated, when a substituent is deemed to be "optionally substituted," or "substituted" it is meant that the substituent is a group that may be substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxy, alkoxy, aryloxy, acyl, ester, mercapto, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. Similarly, the term "optionally ring-halogenated" may be used to refer to a group that optionally contains one or more (e.g., one, two, three or four) halogen substituents on the aryl and/or heteroaryl ring. The protecting groups that may form the protective derivatives of the above substituents are known to those of skill in the art and may be found in references such as Greene and Wuts, Protective Groups in Organic Synthesis, $3^{rd}$ Ed., John Wiley & Sons, New York, N.Y., 1999, which is hereby incorporated by reference in its entirety.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure or be stereoisomeric mixtures. In addition it is understood that, in any compound having one or more double bond(s) generating geometrical isomers that can be defined as E or Z each double bond may independently be E or Z a mixture thereof. Likewise, all tautomeric forms are also intended to be included.

The following abbreviations are used to identify various iodinated compounds. TE stands for tyrosine ethyl ester, DAT stands for desaminotyrosine and DTE for desaminotyrosyl tyrosine ethyl ester. The polymer obtained by phosgenation of DTE is denoted as poly(DTE carbonate). An "I" before the abbreviation shows mono-iodination (e.g. ITE stands for mono-iodinated TE) and an $I_2$ before the abbreviation shows di-iodination (e.g. $I_2$DAT stands for di-iodinated DAT). In DTE, if the "I" is before D, it means the iodine is on DAT and if "I" is after D, it means the iodine is on the tyrosine ring (e.g. $DI_2TE$ stands for DTE with 2 iodine atoms on the tyrosine ring). The following diagram illustrates this nomenclature further.

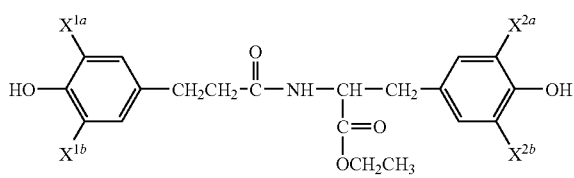

General Structure of Iodinated DTE Monomer

IDTE: $X^{1a}=I, X^{1b}=H, X^{2a}=H, X^{2b}=H$.

$I_2$DTE: $X^{1a}=I, X^{1b}=I, X^{2a}=H, X^{2b}=H$ $DI_2$TE: $X^{1a}=H, X^{1b}=H, X^{2a}=I, X^{2b}=I$

IDITE: $X^{1a}=I, X^{1b}=H, X^{2a}=I, X^{2b}=H$

As used herein, the abbreviations for any protective groups, amino acids and other compounds are, unless indicated otherwise, in accord with their common usage, recognized abbreviations, or the IUPAC-IUP Commission on Biochemical Nomenclature (See, Biochem. 11:942-944 (1972)).

Polymer Compositions and Methods

An embodiment provides a biocompatible polymer composition, comprising at least a first polymer phase and a second polymer phase. In some embodiments the biocompatible polymer composition is bioresorbable, biodegradable, or both. In some embodiments the polymer composition is radiopaque, whereas in other embodiments it is not radiopaque. Some radiopaque polymer compositions comprise a radiopacifying agent in an amount effective to render the polymer composition radiopaque. Other polymer compositions are inherently radiopaque, e.g., contain sufficient halogen atoms attached to one or more of the polymers in the composition to render the composition inherently radiopaque. In some embodiments, the polymer composition is rendered radiopaque by the combination of halogenation of one or more of the polymer constituents and by the inclusion of a radiopacifying agent. In some embodiments the polymer compositions comprises a a biologically active compound (e.g., a drug), which may be dispersed in the polymer composition and/or covalently attached to the first polymer phase, the second polymer phase or both. Various aspects of the aforementioned polymer compositions are described in greater detail below.

The first polymer phase of the biocompatible polymer composition has at least one first wet thermal transition temperature selected from a first wet glass transition temperature and a first wet melting point, where the first wet thermal transition temperature is at least about 38° C. In other embodiments, the first wet thermal transition temperature is at least about 40° C., at least about 45° C., or at least about 50° C. In some embodiments the first polymer phase is crystalline, in other embodiments it is semi-crystalline, and in other embodiments it is glassy. For example, in some embodiments the first polymer phase is at least partially crystalline at a temperature below 37° C., e.g., by selecting the first recurring units of the formula (I) such that the first polymer phase contains sufficient crystallizable side chains to render the first polymer phase at least partially crystalline at a temperature below 37° C.

The first polymer phase comprises a number (n) of first recurring units of the formula (I) as set forth above. In formula (I), $X^1$ and $X^2$ are each independently selected from the group consisting of halogen, halomethyl, halomethoxy, methyl, methoxy, thiomethyl, nitro, sulfoxide, and sulfonyl. The variables $y^1$ and $y^2$ indicate the number of $X^1$ and $X^2$ groups, respectively, and are each independently zero or an integer in the range of 1 to 4. In some embodiments, the first recurring units of the formula (I) are selected to contain sufficient heavy atomes (e.g., halogen atoms) to render the polymer composition inherently radiopaque. For example, routine experimentation may be used to selected $X^1$, $X^2$, $y^1$ and/or $y^2$ so as to render the resulting polymeric material radiopaque.

The variables q and r in formula (I) are each independently zero or one, where q+r=1 or 2. Each $A^1$ in formula (I) is independently selected from the group consisting of

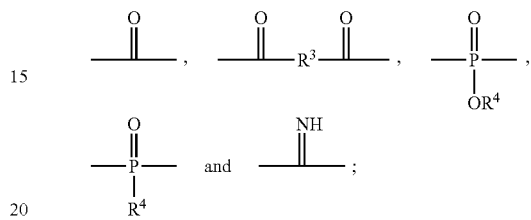

where each $R^3$ is independently selected from the group consisting of $C_1$-$C_{30}$ alkyl, $C_1$-$C_{30}$ heteroalkyl, $C_5$-$C_{30}$ aryl, $C_6$-$C_{30}$ alkylaryl, and $C_2$-$C_{30}$ heteroaryl, and each $R^4$ independently selected from the group consisting of H, $C_1$-$C_{30}$ alkyl, and $C_1$-$C_{30}$ heteroalkyl.

Each $R^1$ in formula (I) is independently selected from the group consisting of

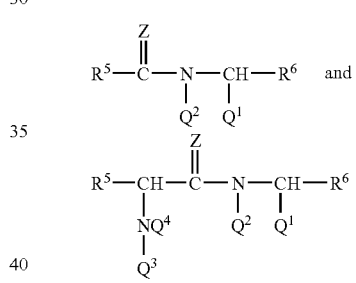

Each $R^1$ may also be an imino-containing unit of the formula:

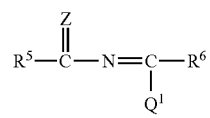

in which case $Q^1$ is $COOR_4$.

Each $R^1$ may also independently be a proline-based unit of the formula

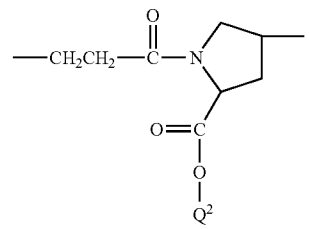

in which case r=0.

Each $R^5$ in the structures depicted above is selected from the group consisting of —CH=CH—, —$CHJ^1$-$CHJ^2$-, —$(CH_2)_a$—, and optionally ring-halogenated

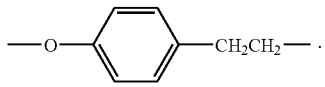

Each $R^5$ in the structures depicted above may also independently be an optionally ring-halogenated tryptophan-based unit of the formula

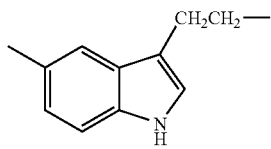

in which case q=0.

Each $R^6$ in the structures depicted above is selected from the group consisting of —CH=CH—, —$CHJ^1$-$CHJ^2$-, —$(CH_2)_a$—, and optionally ring-halogenated

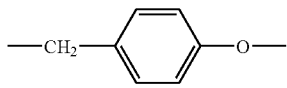

Each $R^6$ in the structures depicted above may also independently be an optionally ring-halogenated tryptophan-based unit of the formula

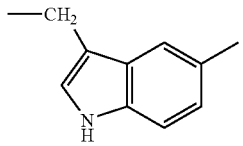

in which case r=0.

Each a in the structures depicted above is independently zero or an integer in the range of 1 to 8; $J^1$ and $J^2$ are each independently selected from the group consisting of Br and I; and each Z is independently an O or an S.

$Q^1$ and $Q^4$ in the structures depicted above are each independently H, $CH_2$—$R^4$, $COOR^4$ or a crystallizable group comprising from about 6 to about 30 carbon atoms, preferably from about 20 to about 30 carbon atoms; and $Q^2$ and $Q^3$ are each independently H, $CH_2$—$R^4$, or a crystallizable group comprising from about 6 to about 30 carbon atoms, preferably from about 20 to about 30 carbon atoms. Examples of various crystallizable groups and a discussion of their preferred spacing along the polymer chain are provided above.

In various embodiments of the recurring units represented by formula (I), q=r=1; $Q^1$ is $COOR^4$; and $Q^2$, $Q^3$, and $Q^4$ are all hydrogen. In some embodiments, q=0. In some embodiments, r=0. In some embodiments, $A^1$ is a carbonyl linkage:

The second polymer phase of the biocompatible polymer composition has at least one second wet thermal transition temperature selected from a second wet glass transition temperature and a second wet melting point. The second wet thermal transition temperature is 36° C. or lower. In some embodiments the second wet thermal transition temperature is 25° C. or lower, 20° C. or lower, or 5° C. or lower. In some embodiments the second polymer phase is crystalline, in other embodiments it is semi-crystalline, and in other embodiments it is glassy. Various second recurring units are described in greater detail below.

The first polymer phase comprises a number (n) of first recurring units of the formula (I) as set forth above, and the second polymer phase comprises a number (m) of second recurring units. The number (n) and the number (m) are selected to control the relative amounts of the first polymer phase and the second polymer phase so that the polymer composition is phase-separated over at least the temperature range of about 25° C. to about 50° C., and preferably over the temperature range of about 10° C. to about 70° C.

Those skilled in the art will understand that the various first recurring units of the formula (I) need not be identical to one another, and thus the number (n) of first recurring units of the formula (I) may include two or more recurring units of the formula (I) that differ from one another in chemical structure Likewise, the various second recurring units in the polymer composition need not be identical to one another, and thus the number (m) of second recurring units may include two or more recurring units that differ from one another in chemical structure. For example, in an embodiment, a polymer composition comprises second recurring units having a formula selected from the group consisting of the formula (IIa), the formula (IIb), the formula (IIc), and the formula (IId). Such a polymer may optionally further comprise third recurring units having a formula that is also selected from the group consisting of the formula (IIa), the formula (IIb), the formula (IIc), and the formula (IId), wherein the third recurring units differ from the second recurring units.

In some embodiments the first polymer phase is covalently attached to the second polymer phase. For example, in an embodiment the polymer composition comprises a block copolymer that includes at least a first block and a second block, wherein the block copolymer is phase-separated so that more than about half of the first block is in the first polymer phase and more than about half of the second block is in the second polymer phase. In some embodiments the first polymer phase is not covalently attached to the second polymer phase. For example, in an embodiment, the first polymer phase comprises a first polymer and the second polymer phase comprises a second polymer that is different from the first polymer.

In an embodiment, the number (n) and the number (m) are selected to control the relative amounts of the first polymer phase and the second polymer phase so that the polymer composition has a water content of 4.5% or less, preferably 3.0% or less, more preferably 2.0% or less, as measured by Karl Fisher analysis after soaking for 24 hours at 37° C. in 0.1 M phosphate buffered saline (PBS) at pH 7.4.

In an embodiment, the number (n) and the number (m) are selected to control the relative amounts of the first polymer phase and the second polymer phase so that the volume fraction of the second polymer phase in the polymer composition is in the range of about 6% to about 40%, e.g., about 7% to about 33%, about 7% to about 26%, about 7% to about 20%, about 7% to about 26%, about 7% to about 16%, about 9% to about 16%, about 9% to about 13%, about 10% to about 13%, or about 10% to about 12%, based on total volume.

In an embodiment, the number (n) and the number (m) are selected to control the relative amounts of the first polymer phase and the second polymer phase so that the weight fraction of the second polymer phase in the polymer composition is in the range of about 6% to about 20%, preferably about 8% to about 18%, preferably about 10% to about 15%, based on total weight.

In an embodiment, the number (n) and the number (m) are selected to control the ductility properties of the polymer composition, such that the polymer composition has an elongation at break of greater than 30%, preferably greater than 50%, more preferably greater than 70%; a Young's modulus of greater than 130 ksi, preferably greater than 180 ksi; and/or a strength at yield of greater than 4.0 ksi, preferably greater than 6.4 ksi. The aforementioned ductility properties are measured when the polymer composition is tested under tensile test conditions that comprise (i) providing a tensile test strip having measurements of 0.2 inches wide, a gauge length of 1.0 inches and a thickness of 0.004 inches, (ii) aging the tensile test strip by soaking it for 7 days at 37° C. in 0.1 M phosphate buffered saline (PBS) at pH 7.4 to provide an aged tensile test strip, and (iii) pulling the aged tensile test strip at a rate of 10 inches per minute while submerged in water at 37° C. Multiple tensile test strips (e.g., 3-5) are tested, and the results averaged. A more detailed description of suitable tensile test conditions is described in the working examples below.

In an embodiment, wherein the number (n) and the number (m) are selected to control the fatigue properties of the polymer composition, such that the polymer composition remains intact for at least 60 minutes, preferably at least 80 minutes, more preferably at least 100 minutes. The aforementioned fatigue properties are measured when the polymer composition is tested under fatigue test conditions that comprise (i) providing a fatigue test strip having measurements of 5.0 mm wide, a gauge length of 15 mm and a thickness of 0.1 mm, (ii) aging the fatigue test strip by soaking it for 7 days at 37° C. in 0.1 M phosphate buffered saline (PBS) at pH 7.4 to provide an aged fatigue test strip, and (iii) subjecting the aged fatigue test strip to oscillating deformation at a frequency of 1.2 Hz under a stress of 10 MPa in single frequency stress mode while submerged in water at 37° C. Multiple fatigue test strips (e.g., 3-5) are tested, and the results averaged. A more detailed description of suitable fatigue test conditions is described in the working examples below.

The second polymer phase in the polymer composition may include various second recurring units. For example, in an embodiment, the second recurring units have a formula selected from the group consisting of the formula (IIa), the formula (IIb), the formula (IIc), and the formula (IId), as set forth above, which may be referred to collectively herein as being of the formula (II).

In the formula (II), the variables $X^3$, $X^4$, $X^5$, $X^7$, $X^8$, $X^9$, $X^{10}$, $X^{11}$, $X^{12}$ and $X^{13}$ are each independently selected from the group consisting of O, S and $NR^{10}$, where $R^{10}$ is selected from hydrogen and an alkyl group containing from one to 30 carbon atoms. In various embodiment, all of the variables $X^3$, $X^4$, $X^5$, $X^7$, $X^8$, $X^9$, $X^{10}$, $X^{11}$, $X^{12}$ and $X^{13}$ and $X^{13}$ are O.

In the formula (IId), the variables $Ar^1$ and $Ar^2$ are phenyl rings optionally substituted with from one to four substituents independently selected from the group consisting of a halogen, a halomethyl, a halomethoxy, a methyl, a methoxy, a thiomethyl, a nitro, a sulfoxide, and a sulfonyl. In an embodiment, the $Ar^1$ and/or $Ar^2$ phenyl rings are substituted with a halogen and/or halogen-containing substituent such as halomethyl and/or halo-methoxy. In an embodiment, the $Ar^1$ and/or $Ar^2$ phenyl rings are substituted with a number of halogen and/or halogen-containing substituents that is effective to render the resulting polymer composition radiopaque. Preferred halogens for rendering polymers radiopaque include bromine and iodine.

In the formula (II), the variables $R^8$ and $R^9$ contain from one to ten carbon atoms each and are independently selected from the group consisting of an optionally substituted alkylene, an optionally substituted heteroalkylene, an optionally substituted alkenylene, and an optionally substituted heteroalkenylene.

The variables g and h in formula (IId) are each independently integers in the range of about 1 to about 500, preferably in the range of about 5 to about 100. Thus, the sum of g+h may be in the range of about 2 to about 1000. In various embodiments, the sum of g+h is greater than about 35, preferably greater than about 40, even more preferably greater than about 50. In various embodiments, the sum of g+h in the range of about 18 to about 26; from about 32 to about 39; from In various embodiments, the recurring units of the formula (IId) result from copolymerizing a hydroxy endcapped poly-caprolactone (PCL) macromer of the following formula:

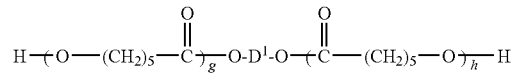

In various embodiments, $D^1$ in formula (IId), and in the hydroxy endcapped poly-caprolactone (PCL) macromer depicted, above is $C_1$-$C_{24}$ alkylene, e.g., —$(CH_2)_t$—, where t is 1, 2, 3, 4, 5, 6, 7, 8, 9, or 10. In various embodiments, g and h are selected for the recurring units of the formula (IId) so that the hydroxy endcapped polycaprolactone (PCL) macromer depicted above has a molecular weight in the range of about 2,000 to about 40,000, e.g., in ranges of about 2,500 to about 3,500; about 4,000 to about 6,000; about 7,000 to about 9,000; about 8,000 to about 12,000; about 18,000 to about 22,000; or about 38,000 to about 46,000.

Embodiments of polymers described herein may be prepared in various ways, e.g., as taught expressly herein or by adapting methods known to those skilled in the art in view of the guidance provided herein. For example, block copolymers may be prepared by reacting a first monomer of the formula (Ia):

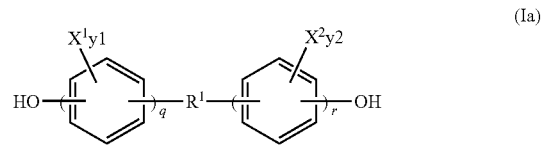

(Ia)

with a second monomer of the formula $HX^8\text{-}D\text{-}X^9H$, the formula $HX^3\text{-}D^1\text{-}X^4H$, the formula

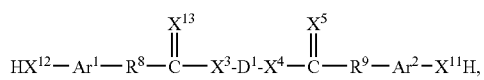

and/or the formula

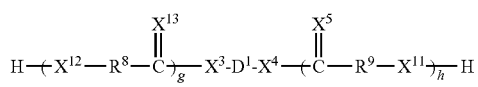

wherein the variables in the above second monomer structures are defined in the same manner as the corresponding polymers described herein. As described above, D, $X^8$ and $X^9$ may be selected so that $HX^8D\text{-}X^9H$ defines a hydroxyl endcapped macromer, a mercapto endcapped macromer or an amino endcapped macromer Likewise, $D^1$, $X^3$ and $X^4$ may be selected so that $HX^3\text{-}D^1\text{-}X^4H$ defines a hydroxyl endcapped macromer, a mercapto endcapped macromer or an amino endcapped macromer. For example, $HX^3\text{-}D^1\text{-}X^4H$ and $HX^8\text{-}D\text{-}X^9H$ may each independently represent a macromer selected from a hydroxy endcapped polylactic acid macromer, a hydroxy endcapped polyglycolic acid macromer, a hydroxy endcapped poly(lactic acid-co-glycolic acid) macromer, a hydroxy endcapped poly-caprolactone macromer, a poly(alkylene diol) macromer, a hydroxy end-capped poly (alkylene oxide) macromer and a hydroxy endcapped polydioxanone macromer.

Those skilled in the art will recognize that by selecting a monomer of formula (Ia) having the appropriate variable groups, the first recurring units of the resulting polymer are tyrosine-derived diphenol repeating units. The diphenol monomers may be prepared by means of carbodiimide-mediated coupling reactions in the presence of hydroxybenzotriazole according to the procedure disclosed in U.S. Pat. Nos. 5,587,507 and 5,670,602, the disclosures of both of which are hereby incorporated by reference. Suitable carbodiimides are disclosed therein. The preferred carbodiimide is 1-ethyl-3-(3-dimethylamino-propyl) carbodiimide hydrochloride (EDCI.HCl). The crude monomers can be recrystallized twice, first from 50% acetic acid and water and then from a 20:20:1 ratio of ethyl acetate, hexane and methanol, or, alternatively, flash chromatography on silica gel is used, employing a 100:2 mixture of methylene chloride:methanol as the mobile phase. The preferred monomers are desaminotyrosyl-tyrosine esters, including the ethyl, butyl, hexyl, octyl and benzyl esters.

In certain embodiments, some of the endcapped macromers, such as hydroxy endcapped polycaprolactone and poly(ethylene glycol), are commercially available. In some cases when endcapped macromers such as hydroxy endcapped poly(lactic acid) are not available, they may be prepared using an alkane diol as the initiator.

Monomers of the formula

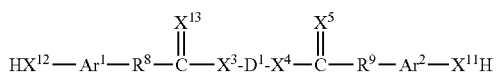

may be prepared by reacting approximately two moles of one or more compounds of the formula

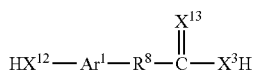

with approximately one mole of a compound of the formula $HX^3\text{-}D^1\text{-}X^4H$, wherein the variables are defined in the same manner as described elsewhere herein.

Those skilled in the art will recognize that by appropriate selection of variable groups, the compound described above is a hydroxyphenyl-alkanoic acid, such as desaminotyrosyl tyrosine (DAT), or a hydroxyphenylalkenoic acid. When the compound of the formula $HX^3\text{-}D^1\text{-}X^4H$ is a diol, the two compounds may be reacted in an acid catalyzed Fischer esterification reaction, illustrated generally as follows:

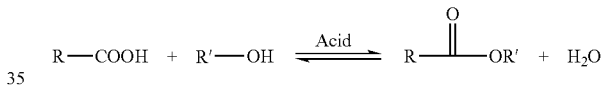

Because this reaction is reversible, removing water from the reaction mixture shifts the equilibrium to the right. Water removal is usually accomplished by way of azeotropic distillation, however other techniques known in the art may be employed as well. In instances where azeotropic distillation is desired, the solvent used for the reaction is preferably carefully chosen so that it forms an azeotropic mixture with water. Generally, solvents such as toluene, heptane, chloroform, tetrachloethylene are preferred.

The main advantage of this reaction is that primary and secondary alcohols form esters with carboxylic acids under acid catalysis, whereas the phenolic hydroxy groups are unreactive under these conditions. Thus the carboxylic acid groups of certain compounds, such as the 3-(4-hydroxyphenyl) propionic acid (DAT) and of 3-(3,5-diiodo-4-hydroxyphenyl) propionic acid ($I_2$DAT), can be reacted with primary or secondary alcohols while the phenolic groups remain intact. An example of the foregoing is as follows:

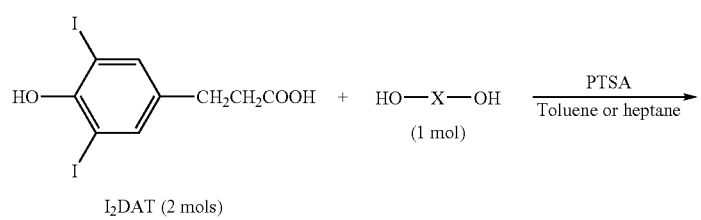

-continued

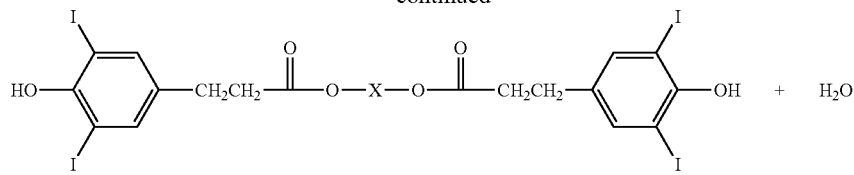

The X group in the foregoing is representative of the D and $D^1$ groups described above. HO—X—OH can be a alkane diol such as 1,3-propane-diol or a hydroxy endcapped macromer as described above.

Polymers with a sufficient number of aromatic rings that are sufficiently substituted with bromine or iodine are inherently radiopaque. Various aromatic rings in both the first polymer phase and the second polymer phase can be iodine or bromine substituted. For example, independent of any particular polymer embodiment, the aromatic rings of the recurring units of the formula (I) may be substituted with at least one iodine or bromine atom, on at least one and preferably on both ring positions. In an embodiment, at least 50% of the aromatic rings of recurring units of the formula (I) in a polymer composition are substituted with from two to four iodine or bromine atoms.

The radiopaque monomers may be prepared according to the disclosure of U.S. Pat. No. 6,475,477, as well as the disclosure of U.S. Patent Publication No. 20060034769, the disclosures of both of which are incorporated herein by reference, and particularly for the purpose of describing such monomers and methods of making them. Iodinated and brominated phenolic monomers described herein can also be employed as radiopacifying, bio-compatible non-toxic additives for biocompatible polymer compositions, as provided herein.

When the first monomer is a tyrosine derived diphenol compound and the second monomer is a dihydroxy monomer (such as a diol or hydroxyl-encapped macromer) the monomers can be polymerized to form polycarbonates. Suitable processes, associated catalysts and solvents are known in the art and are taught in Schnell, Chemistry and Physics of Polycarbonates, (Interscience, New York 1964), the teachings of which are also incorporated herein by reference. Because $X^3$, $X^4$, $X^5$, $X^7$, $X^8$, $X^9$, $X^{10}$, $X^{11}$, $X^{12}$ and $X^{13}$ are each independently selected from the group consisting of O, S and $NR^{10}$ the reaction of the corresponding monomers with phosgene may also produce urethane linkages (—$NR^{10}$—(C=O)—$NR^{10}$—), carbonodithioate linkages (—S—(C=O)—S—), carbamate linkages (—O—(C=O)—$NR^{10}$—), thiocarbonate linkages (—S—(C=O)—O—) and thiocarbamate linkages (—S—(C=O)—$NR^{10}$—). Other methods adaptable for use to prepare the polycarbonate and other phosgene-derived polymers disclosed herein are disclosed in U.S. Pat. Nos. 6,120,491, and 6,475,477, the disclosures of which are incorporated by reference, and particularly for the purpose of describing such methods.

The polycarbonates and other phosgene-derived polymers may also be prepared by dissolving the monomers in methylene chloride containing 0.1M pyridine or triethylamine. A solution of phosgene in toluene at a concentration between about 10 and about 25 wt %, and preferably about 20 wt %, is added at a constant rate, typically over about two hours, using a syringe pump or other means. The reaction mixture is quenched by stirring with tetrahydrofuran (THF) and water, after which the polymer is isolated by precipitation with isopropanol. Residual pyridine (if used) is then removed by agitation of a THF polymer solution with a strongly acidic resin, such as AMBERLYST 15.

Polymer compositions as described herein also include polyethers, polyesters, polyiminocarbonates, polyphosphoesters and polyphosphazines. Those skilled in the art can prepare these polymers using routine experimentation informed by the guidance provided herein. Polyesters, specifically poly(ester amides), may be prepared by the process disclosed by U.S. Pat. No. 5,216,115, the disclosure of which is incorporated by reference, and particularly for the purpose of describing such processes. Polyiminocarbonates may be prepared by the process disclosed by U.S. Pat. No. 4,980,449, the disclosure of which is incorporated by reference, and particularly for the purpose of describing such processes. Polyethers may be prepared by the process disclosed by U.S. Pat. No. 6,602,497, the disclosure of which is incorporated by reference, and particularly for the purpose of describing such processes.

Preferred polymers include those having pendent free carboxylic acid groups ($R_4$=H). However, it is difficult to prepare polymers having pendent free carboxylic acid groups by polymerization of corresponding monomers with pendent free carboxylic acid groups without cross-reaction of the free carboxylic acid group with the co-monomer. Accordingly, polymers having pendent free carboxylic acid groups are preferably prepared from the corresponding benzyl and tert-butyl ester polymers ($R_4$ is a benzyl or tert-butyl group).

The benzyl ester polymers may be converted to the corresponding free carboxylic acid polymers through the selective removal of the benzyl groups by the palladium catalyzed hydrogenolysis method disclosed in U.S. Pat. No. 6,120,491, the disclosure of which is incorporated herein by reference, and particularly for the purpose of describing such methods. The tert-butyl ester polymers may be converted to the corresponding free carboxylic acid polymers through the selective removal of the tert-butyl groups by the acidolyis method disclosed in U.S. Patent Publication No. 20060034769, also incorporated herein by reference, and particularly for the purpose of describing such methods. The catalytic hydrogenolysis or acidolysis is preferable because the lability of the polymer backbone tends to discourage the employment of harsher hydrolysis techniques.

The molar fraction of free carboxylic acid units in the polymers described herein can be adjusted to modify the degradation of devices made from such polymers. For example, polymers with lower amounts of free carboxylic acid will tend to have longer lifetimes in the body. Further, by otherwise adjusting the amount of free carboxylic acid in the polymers across the range of preferred molar fraction, the resulting polymers can be adapted for use in various applications requiring different device lifetimes. In general, the higher the molar fraction of free carboxylic acid units, the shorter the lifetime of the device in the body and more suitable such devices are for applications wherein shorter lifetimes are desirable or required.

Polymer and monomer embodiments derived from diphenol monomers of Formula Ia in which $R^1$ has the imino-containing structure:

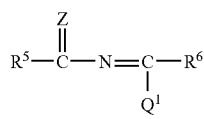

are prepared by methods disclosed by U.S. Provisional Application Ser. No. 61/250,545, filed on the same date as the present application, the disclosure of which is incorporated herein by reference, and particularly for the purpose of describing such methods. More specifically, polymers and monomers with amide groups, i.e., acylamino groups, and a carboxylate group substituted on the carbon that is alpha to the amide nitrogen, are reacted with phosgene or triphosgene in pyridine to form an imino group. In the preparation of polycarbonates, this is simply a matter of reacting the monomer with excess phosgene or tri-phosgene to form the imino group. However, for the preparation of other polymers, the imino group must be formed in advance on the monomer.

As an example, the preparation of $I_2DTE$ thio-imine is depicted by the following reaction scheme:

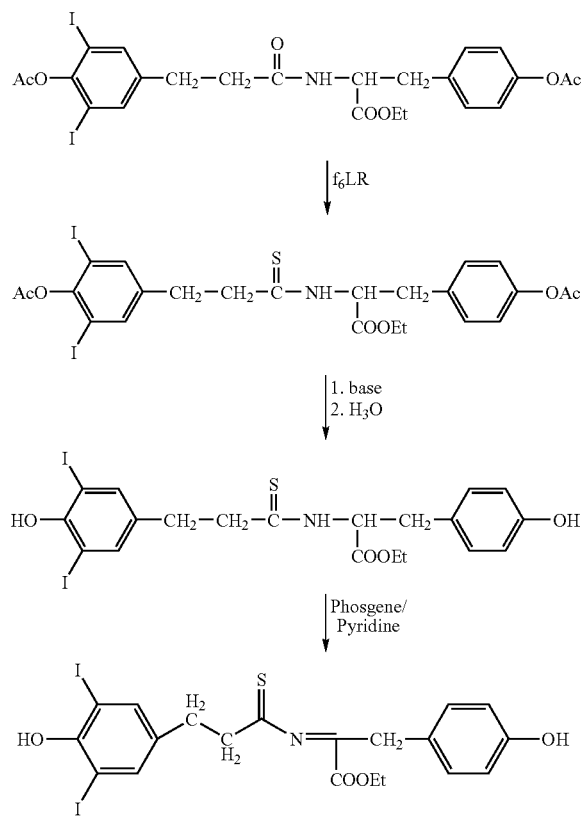

Medical Uses

Various embodiments of the polymer compositions described herein, preferably derived from tissue compatible monomers, may be used to produce a variety of useful articles with valuable physical and chemical properties. The useful articles can be shaped by conventional polymer thermo-forming techniques such as extrusion and injection molding when the degradation temperature of the polymer is above the glass transition or crystalline melt temperature(s), or conventional non-thermal techniques can be used, such as compression molding, injection molding, solvent casting, spin casting, wet spinning. Combinations of two or more methods can be used. Shaped articles prepared from the polymers are useful, inter alia, as biocompatible, biodegradable and/or bioresorbable biomaterials for medical implant applications.

In one embodiment, the medical device is a stent. It is contemplated that a stent may comprise many different types of forms. For instance, the stent may be an expandable stent.

In another embodiment, the stent may be configured to have the form of a sheet stent, a braided stent, a self-expanding stent, a woven stent, a deformable stent, or a slide-and-lock stent. Stent fabrication processes may further include two-dimensional methods of fabrication such as cutting extruded sheets of polymer, via laser cutting, etching, mechanical cutting, or other methods, and assembling the resulting cut portions into stents, or similar methods of three-dimensional fabrication of devices from solid forms.

In certain other embodiments, the polymers are formed into coatings on the surface of an implantable device, particularly a stent, made either of a polymer as described herein or another material, such as metal. Such coatings may be formed on stents via techniques such as dipping, spray coating, combinations thereof, and the like. Further, stents may be comprised of at least one fiber material, curable material, laminated material and/or woven material. The medical device may also be a stent graft or a device used in embolotherapy.

Details of stent products and fabrication in which the polymers described herein may be employed are disclosed in U.S. Patent Publication No. 20060034769, the disclosure of which is incorporated by reference, and particularly for the purpose of describing such stent products and fabrication methods. Stents are preferably fabricated from the radiopaque polymers described herein, to permit fluoroscopic positioning of the device.

The highly beneficial combination of properties associated with preferred embodiments of the polymers described herein means these polymers are well-suited for use in producing a variety of resorbable medical devices besides stents, especially implantable medical devices that are preferably radiopaque, biocompatible, and have various times of bioresorption. For example the polymers are suitable for use in resorbable implantable devices with and without therapeutic agents, device components and/or coatings with and without therapeutic agents for use in other medical systems, for instance, the musculoskeletal or orthopedic system (e.g., tendons, ligaments, bone, cartilage skeletal, smooth muscles); the nervous system (e.g., spinal cord, brain, eyes, inner ear); the respiratory system (e.g., nasal cavity and sinuses, trachea, larynx, lungs); the reproductive system (e.g., male or female reproductive); the urinary system (e.g., kidneys, bladder, urethra, ureter); the digestive system (e.g., oral cavity, teeth, salivary glands, pharynx, esophagus, stomach, small intestine, colon), exocrine functions (biliary tract, gall bladder, liver, appendix, recto-anal canal); the endocrine system (e.g., pancreas/islets, pituitary, parathyroid, thyroid, adrenal and pineal body), the hematopoietic system (e.g., blood and bone marrow, lymph nodes, spleen, thymus, lymphatic vessels); and, the integumentary system (e.g., skin, hair, nails, sweat glands, sebaceous glands).

The polymers described herein can thus be used to fabricate wound closure devices, hernia repair meshes, gastric lap bands, drug delivery implants, envelopes for the implantation of cardiac devices, devices for other cardiovascular applications, non-cardiovascular stents such as biliary stents, esophageal stents, vaginal stents, lung-trachea/bronchus stents, and the like.

In addition, the resorbable polymers are suitable for use in producing implantable, radiopaque discs, plugs, and other devices used to track regions of tissue removal, for example, in the removal of cancerous tissue and organ removal, as well as, staples and clips suitable for use in wound closure, attaching tissue to bone and/or cartilage, stopping bleeding (homeostasis), tubal ligation, surgical adhesion prevention, and the like. Applicants have also recognized that preferred embodiments of the polymers described herein are well-suited for use in producing a variety of coatings for medical devices, especially implantable medical devices.

Further, in some preferred embodiments, the present polymers may be advantageously used in making various resorbable orthopedic devices including, for example, radiopaque biodegradable screws (interference screws), radiopaque biodegradable suture anchors, and the like for use in applications including the correction, prevention, reconstruction, and repair of the anterior cruciate ligament (ACL), the rotator cuff/rotator cup, and other skeletal deformities.

Other devices that can be advantageously formed from preferred embodiments of the polymers described herein, include devices for use in tissue engineering. Examples of suitable resorbable devices include tissue engineering scaffolds and grafts (such as vascular grafts, grafts or implants used in nerve regeneration). The resorbable polymers may also be used to form a variety of devices effective for use in closing internal wounds. For example biodegradable resorbable sutures, clips, staples, barbed or mesh sutures, implantable organ supports, and the like, for use in various surgery, cosmetic applications, and cardiac wound closures can be formed.

Various devices useful in dental applications may advantageously be formed according to embodiments of the described herein. For example devices for guided tissue regeneration, alveolar ridge replacement for denture wearers, and devices for the regeneration of maxilla-facial bones may benefit from being radiopaque so that the surgeon or dentist can ascertain the placement and continuous function of such implants by simple X-ray imaging.

Preferred embodiments of the polymers described herein are also useful in the production of bioresorbable, inherently radiopaque polymeric embolotherapy products for the temporary and therapeutic restriction or blocking of blood supply to treat tumors and vascular malformations, e.g., uterine fibroids, tumors (i.e., chemoembolization), hemorrhage (e.g., during trauma with bleeding) and arteriovenous malformations, fistulas and aneurysms delivered by means of catheter or syringe. Details of embolotherapy products and methods of fabrication in which the polymers described herein may be employed are disclosed in U.S. Patent Publication No. 20050106119 A1, the disclosure of which is incorporated by reference, and particularly for the purpose of describing such products and methods. Embolotherapy treatment methods are by their very nature local rather than systemic and the products are preferably fabricated from the radio-opaque polymers described herein, to permit fluoroscopic monitoring of delivery and treatment.

The polymers described herein are further useful in the production of a wide variety of therapeutic agent delivery devices. Such devices may be adapted for use with a variety of therapeutics including, for example, pharmaceuticals (i.e., drugs) and/or biological agents as previously defined and including biomolecules, genetic material, and processed biologic materials, and the like. Any number of transport systems capable of delivering therapeutics to the body can be made, including devices for therapeutics delivery in the treatment of cancer, intravascular problems, dental problems, obesity, infection, and the like.

A medical device that comprises a polymeric material may include one or more additional components, e.g., a plasticizer, a filler, a crystallization nucleating agent, a preservative, a stabilizer, a photoactivation agent, etc., depending on the intended application. For example, in an embodiment, a medical device comprises an effective amount of at least one therapeutic agent and/or a magnetic resonance enhancing agent. Non-limiting examples of preferred therapeutic agents include a chemotherapeutic agent, a non-steroidal anti-inflammatory, a steroidal anti-inflammatory, and a wound healing agent. Therapeutic agents may be co-administered with the polymeric material. In a preferred embodiment, at least a portion of the therapeutic agent is contained within the polymeric material. In another embodiment, at least a portion of the therapeutic agent is contained within a coating on the surface of the medical device.

Non-limiting examples of preferred chemotherapeutic agents include taxanes, taxinines, taxols, paclitaxel, dioxorubicin, cis-platin, adriamycin, and bleomycin. Non-limiting examples of preferred non-steroidal anti-inflammatory compounds include aspirin, dexa-methasone, ibuprofen, naproxen, and Cox-2 inhibitors (e.g., Rofexcoxib, Celecoxib and Valdecoxib). Non-limiting examples of preferred steroidal anti-inflammatory compounds include dexamethasone, beclomethasone, hydrocortisone, and prednisone. Mixtures comprising one or more therapeutic agents may be used. Non-limiting examples of preferred magnetic resonance enhancing agents include gadolinium salts such as gadolinium carbonate, gadolinium oxide, gadolinium chloride, and mixtures thereof.

The amounts of additional components present in the medical device are preferably selected to be effective for the intended application. For example, a therapeutic agent is preferably present in the medical device in an amount that is effective to achieve the desired therapeutic effect in the patient to whom the medical device is administered or implanted. Such amounts may be determined by routine experimentation. In certain embodiments, the desired therapeutic effect is a biological response. In an embodiment, the therapeutic agent in the medical device is selected to promote at least one biological response, preferably a biological response selected from the group consisting of thrombosis, cell attachment, cell proliferation, attraction of inflammatory cells, deposition of matrix proteins, inhibition of thrombosis, inhibition of cell attachment, inhibition of cell proliferation, inhibition of inflammatory cells, and inhibition of deposition of matrix proteins. The amount of magnetic resonance enhancing agent in a medical devices is preferably an amount that is effective to facilitate radiologic imaging, and may be determined by routine experimentation.

The term "pharmaceutical agent", as used herein, encompasses a substance intended for mitigation, treatment, or prevention of disease that stimulates a specific physiologic (metabolic) response. The term "biological agent", as used herein, encompasses any substance that possesses structural and/or functional activity in a biological system, including without limitation, organ, tissue or cell based derivatives, cells, viruses, vectors, nucleic acids (animal, plant, microbial, and viral) that are natural and recombinant and synthetic in origin and of any sequence and size, antibodies, polynucleotides, oligonucleotides, cDNA's, oncogenes, proteins, peptides, amino acids, lipoproteins, glycoproteins, lipids, carbohydrates, polysaccharides, lipids, liposomes, or other cellular components or organelles for instance receptors and ligands. Further the term "biological agent", as used herein, includes virus, serum, toxin, antitoxin, vaccine, blood, blood component or derivative, allergenic product, or analogous product, or arsphenamine or its derivatives (or any trivalent organic arsenic compound) applicable to the prevention, treatment, or cure of diseases or injuries of man (per Section 351(a) of the Public Health Service Act (42 U.S.C. 262(a)). Further the term "biological agent" may include 1) "biomolecule", as used herein, encompassing a biologically active peptide, protein, carbohydrate, vitamin, lipid, or nucleic acid produced by and purified from naturally occurring or recombinant organisms, antibodies, tissues or cell lines or synthetic analogs of such molecules; 2) "genetic material" as used herein, encompassing nucleic acid (either deoxyribonucleic acid (DNA) or ribonucleic acid (RNA), genetic element, gene, factor, allele, operon, structural gene, regulator gene, operator gene, gene complement, genome, genetic code, codon, anticodon, messenger RNA (mRNA), transfer RNA (tRNA), ribosomal extrachromosomal genetic element, plasmagene, plasmid, transposon, gene mutation, gene sequence, exon, intron, and, 3) "processed biologics", as used herein, such as cells, tissues or organs that have undergone manipulation. The therapeutic agent may also include vitamin or mineral substances or other natural elements.

For devices placed in the vascular system, e.g., a stent, the amount of the therapeutic agent is preferably sufficient to inhibit restenosis or thrombosis or to affect some other state of the stented tissue, for instance, heal a vulnerable plaque, and/or prevent rupture or stimulate endothelialization. The agent(s) may be selected from the group consisting of anti-proliferative agents, anti-inflammatory, anti-matrix metalloproteinase, and lipid lowering, cholesterol modifying, anti-thrombotic and antiplatelet agents, in accordance with preferred embodiments of the present invention. In some preferred embodiments of the stent, the therapeutic agent is contained within the stent as the agent is blended with the polymer or admixed by other means known to those skilled in the art. In other preferred embodiments of the stent, the therapeutic agent is delivered from a polymer coating on the stent surface. In another preferred variation the therapeutic agent is delivered by means of no polymer coating. In other preferred embodiments of the stent, the therapeutic agent is delivered from at least one region or one surface of the stent. The therapeutic may be chemically bonded to the polymer or carrier used for delivery of the therapeutic of at least one portion of the stent and/or the therapeutic may be chemically bonded to the polymer that comprises at least one portion of the stent body. In one preferred embodiment, more than one therapeutic agent may be delivered.

In certain embodiments, any of the aforementioned devices described herein can be adapted for use as a therapeutic delivery device (in addition to any other functionality thereof). Controlled therapeutic delivery systems may be prepared, in which a therapeutic agent, such as a biologically or pharmaceutically active and/or passive agent, is physically embedded or dispersed within a polymeric matrix or physically admixed with a polymer described herein. Controlled therapeutic agent delivery systems may also be prepared by direct application of the therapeutic agent to the surface of an implantable medical device such as a bioresorbable stent device (comprised of at least one of the polymers described herein) without the use of these polymers as a coating, or by use of other polymers or substances for the coating.

When $R^4$ is hydrogen the $COOR^4$ pendant groups of embodiments of the polymers described herein may also be derivatized by covalent attachment of a therapeutic agent. Depending on the moieties present on the underivatized therapeutic agent the covalent bond may be an amide or ester bond. Typically the therapeutic agent is derivatized at a primary or secondary amine, hydroxy, ketone, aldehyde or carboxylic acid group. Chemical attachment procedures are described by U.S. Pat. Nos. 5,219,564 and 5,660,822; Nathan et al., Bio. Cong. Chem., 4, 54-62 (1993) and Nathan, Macromol., 25, 4476 (1992), all of which are incorporated by reference, and particularly for the purpose of describing such procedures.

The therapeutic agent may first be covalently attached to a monomer, which is then polymerized, or the polymerization may be performed first, followed by covalent attachment of the therapeutic agent. Hydrolytically stable conjugates are utilized when the therapeutic agent is active in conjugated form. Hydrolyzable conjugates are utilized when the therapeutic agent is inactive in conjugated form.

Therapeutic agent delivery compounds may also be formed by physically blending the therapeutic agent to be delivered with the polymers described herein using conventional techniques well-known to those of ordinary skill in the art. For this therapeutic agent delivery embodiment, it is not essential that the polymer have pendent groups for covalent attachment of the therapeutic agent.

The polymer compositions described herein containing therapeutic agents, regardless of whether they are in the form of polymer conjugates or physical admixtures of polymer and therapeutic agent, are suitable for applications where localized delivery is desired, as well as in situations where a systemic delivery is desired. The polymer conjugates and physical admixtures may be implanted in the body of a patient in need thereof, by procedures that are essentially conventional and well-known to those of ordinary skill in the art.

Implantable medical devices may thus be fabricated that also serve to deliver a therapeutic agent to the site of implantation by being fabricated from or coated with the therapeutic agent delivery system described herein in which a polymer has a therapeutic agent physically admixed therein or covalently bonded thereto, such as a drug-eluting stent. Embolotherapeutic particles may also be fabricated for delivery of a therapeutic agent.

Examples of biologically or pharmaceutically active therapeutic agents that may be covalently attached to the polymers described herein include acyclovir, cephradine, malphalen, procaine, ephedrine, adriamycin, daunomycin, plumbagin, atropine, quinine, digoxin, quinidine, biologically active peptides, chlorin e.sub.6, cephradine, cephalothin, proline and proline analogs such as cis-hydroxy-L-proline, malphalen, penicillin V and other antibiotics, aspirin and other non-steroidal anti-inflammatories, nicotinic acid, chemodeoxycholic acid, chlorambucil, anti-tumor and anti-proliferative agents, including anti-proliferative agents that prevent restenosis, hormones such as estrogen, and the like. Biologically active compounds, for the purposes of the present invention, are additionally defined as including cell attachment mediators, biologically active ligands, and the like.

The invention described herein also includes various pharmaceutical dosage forms containing the polymer-therapeutic agent combinations described herein. The combination may be a bulk matrix for implantation or fine particles for administration by traditional means, in which case the dosage forms include those recognized conventionally, e.g. tablets, capsules, oral liquids and solutions, drops, parenteral solutions and suspensions, emulsions, oral powders, inhalable solutions or powders, aerosols, topical solutions, suspensions, emulsions, creams, lotions, ointments, transdermal liquids and the like.

The dosage forms may include one or more pharmaceutically acceptable carriers. Such materials are non-toxic to recipients at the dosages and concentrations employed, and include diluents, solubilizers, lubricants, suspending agents, encapsulating materials, penetration enhancers, solvents, emollients, thickeners, dispersants, buffers such as phosphate, citrate, acetate and other organic acid salts, antioxidants such as ascorbic acid, preservatives, low molecular weight (less than about 10 residues) peptides such as polyarginine, proteins such as serum albumin, gelatin, or immunoglobulins, other hydrophilic polymers such as poly(vinylpyrrolidinone), amino acids such as glycine, glutamic acid, aspartic acid, or arginine, monosaccharides, disaccharides, and other carbohydrates, including cellulose or its derivatives, glucose, mannose, or dextrines, chelating agents such as EDTA, sugar alcohols such as mannitol or sorbitol, counterions such as sodium and/or nonionic surfactants such as tween, pluronics or PEG.

Therapeutic agents to be incorporated in the polymer compositions and physical admixtures described herein may be provided in a physiologically acceptable carrier, excipient stabilizer, etc., and may be provided in sustained release or timed release formulations supplemental to the polymeric compositions described herein. Liquid carriers and diluents for aqueous dispersions are also suitable for use with the polymer compositions and physical admixtures.

Subjects in need of treatment, typically mammalian, using the polymer-therapeutic agent combinations described herein, can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize. The polymer-therapeutic agent combinations described herein may be prepared for storage under conditions suitable for the preservation of therapeutic agent activity as well as maintaining the integrity of the polymers, and are typically suitable for storage at ambient or refrigerated temperatures.

Depending upon the particular compound selected transdermal delivery may be an option, providing a relatively steady delivery of the drug, which is preferred in some circumstances. Transdermal delivery typically involves the use of a compound in solution, with an alcoholic vehicle, optionally a penetration enhancer, such as a surfactant, and other optional ingredients. Matrix and reservoir type transdermal delivery systems are examples of suitable transdermal systems. Transdermal delivery differs from conventional topical treatment in that the dosage form delivers a systemic dose of the therapeutic agent to the patient.

The polymer-drug formulations described herein may also be administered in the form of liposome delivery systems, such as small unilamellar vesicles, large unilamellar vesicles and multilamellar vesicles. Liposomes may be used in any of the appropriate routes of administration described herein. For example, liposomes may be formulated that can be administered orally, parenterally, transdermally or via inhalation. Therapeutic agent toxicity could thus be reduced by selective delivery to the affected site. For example if the therapeutic agent is liposome encapsulated, and is injected intravenously, the liposomes used are taken up by vascular cells and locally high concentrations of the therapeutic agent could be released over time within the blood vessel wall, resulting in improved action of the therapeutic agent. The liposome encapsulated therapeutic agents are preferably administered parenterally, and particularly, by intravenous injection.

Liposomes may be targeted to a particular site for release of the therapeutic agent. This would obviate excessive dosages that are often necessary to provide a therapeutically useful dosage of a therapeutic agent at the site of activity, and consequently, the toxicity and side effects associated with higher dosages.

Therapeutic agents incorporated into the polymers described herein may desirably further incorporate agents to facilitate their delivery systemically to the desired target, as long as the delivery agent meets the same eligibility criteria as the therapeutic agents described above. The active therapeutic agents to be delivered may in this fashion be incorporated with antibodies, antibody fragments, growth factors, hormones, or other targeting moieties, to which the therapeutic agent molecules are coupled.

The polymer-therapeutic agent combinations described herein may also be formed into shaped articles, such as valves, stents, tubing, prostheses, and the like. Cardiovascular stents may be combined with therapeutic agents that prevent restenosis. Implantable medical devices may be combined with therapeutic agents that prevent infection.

Therapeutically effective dosages may be determined by either in vitro or in vivo methods. For each particular drug, individual determinations may be made to determine the optimal dosage required. The range of therapeutically effective dosages will naturally be influenced by the route of administration, the therapeutic objectives, and the condition of the patient. For the various suitable routes of administration, the absorption efficiency must be individually determined for each drug by methods well known in pharmacology. Accordingly, it may be necessary for the therapist to titer the dosage and modify the route of administration as required to obtain the optimal therapeutic effect.

The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved. The release rate from the formulations described herein are also varied within the routine skill in the art to determine an advantageous profile, depending on the therapeutic conditions to be treated.

A typical dosage might range from about 0.001 mg/k/g to about 1,000 mg/k/g, preferably from about 0.01 mg/k/g to about 100 mg/k/g, and more preferably from about 0.10 mg/k/g to about 20 mg/k/g. Advantageously, the polymer-therapeutic agent combinations described herein may be administered several times daily, and other dosage regimens may also be useful.

In practicing the methods described herein, the polymer-therapeutic agent combinations may be used alone or in combination with other therapeutic or diagnostic agents. The polymer-therapeutic agent combinations described herein can be utilized in vivo, ordinarily in mammals such as primates such as humans, sheep, horses, cattle, pigs, dogs, cats, rats and mice, or in vitro.

An advantage of using the radiopaque, bioresorbable polymers described herein in therapeutic agent delivery applications is the ease of monitoring release of a therapeutic agent and the presence of the implantable therapeutic delivery system. Because the radiopacity of the polymeric matrix is due to covalently attached halogen substituents, the level of radiopacity is directly related to the residual amount of the degrading therapeutic agent delivery matrix still present at the implant site at any given time after implantation. In preferred embodiments the rate of therapeutic release from the degrading therapeutic delivery system will be correlated with the rate of polymer resorption. In such preferred embodiments, the straight-forward, quantitative measurement of the residual degree of radio-opacity will provide the attending physician with a way to monitor the level of therapeutic release from the implanted therapeutic delivery system.

The following non-limiting examples set forth herein below illustrate certain aspects of the invention. All parts and percentages are by mole percent unless otherwise noted and all temperatures are in degrees Celsius unless otherwise indicated. All solvents were HPLC grade and all other reagents were of analytical grade and used as received, unless otherwise indicated.

EXAMPLES

Preparation Example 1

$I_2$DAT Macromer ($I_2$DAT Diester of 1,5-Pentane Diol)

In a 500 mL flask equipped with overhead stirrer and Dean-stark trap were placed 1,5-pentane diol (8.75 g, 84 mmol), $I_2$DAT (71 g, 0.17 mol), 4-toluenesulfonic acid (1.6 g, 8.4 mmol) and 200 mL heptane. A nitrogen inlet adopter was placed on top of the condenser to maintain nitrogen atmosphere. The flask was heated using a heating mantle. The water collected was periodically measured and the reflux continued until the theoretical amount of water collected. More water than expected may be collected due to water present in the reagents. The reaction was stopped when the water evolution stopped. The heptane turned pink to purple due to trace quantities of iodine liberated. The reaction mixture was allowed to cool with stirring. The crude product was collected by filtration. For purification the crude product was dissolved in 100 mL of acetone. To the solution was added with stirring 400 mL of 5% $NaHCO_3$ solution and stirring was continued until the product crystallized. The macromer product was collected by filtration and washed with 50 mL of 5% $NaHCO_3$ solution followed by 2×50 mL of DI water. The macromer product was dried in a vacuum oven and characterized by $^1$H NMR and HPLC. The macromer product was characterized by $^1$H NMR and GPC. The molecular weight (GPC, polystyrene standards) was 10,000.

Similar procedures were used to prepare macromeric $I_2$DAT di-esters of hexanediol and propanediol.

Preparation Example 2

Hydroxy-Endcapped PLLA Macromer

The three reagents In a 100 mL round bottom flask were placed 1,3-propanediol (1.02 g, 13.4 mmol), L-lactide (36.3 g, 252 mmol) and Stannous Octoate (0.5 g, 1.26 mmol). The contents of the flask were stirred and dried under vacuum. The flask was then lowered into a silicon oil bath whose temperature was maintained between 130-140° C. The lactide began to melt and a clear liquid resulted. When observed after 2 h the reaction mixture was opaque (white), still liquid at about 130° C. The materials were allowed to react for 24 h. On cooling a white solid was obtained. The $^1$H NMR showed the absence of unreacted 1,3-propanediol. GPC with THF as mobile phase (GPC, polystyrene standards) showed a bi-modal peak with Mn=3800 and Mw=7500.

Preparation Example 3

Polymerization of PLLA-Diol Using Triphosgene

Into a 250 mL round bottomed flask were added 7.50 g (0.005 mol) of PLLA-diol of Mn 1500. To the flask were also added 60 mL of methylene chloride and 1.53 g (0.019 mol) of pyridine and stirred with an overhead stirrer. To the resulting clear solution was slowly added over a period of 2 hours, 0.42 g (0.006 equivalent of phosgene) of triphosgene in 2 mL of methylene chloride, using a syringe pump. After stirring for 15 min, GPC showed a MW of 60,000. Reaction mixture washed twice with 0.2 M HCl and then precipitated with methanol. The initially formed viscous oil solidified after stirring for 1 hours into a white crystalline solid. This was dried in vacuum oven at 40° C. for 24 hours.

Preparation Example 4

Poly(PHMC2K Carbonate) Diol

In a 1 L 4-necked flask with overhead stirrer were placed 53.4 g (27 mmol) of poly(hexamethylene carbonate 2000) (PHMC2K), 200 mL of methylene chloride and 8.23 g (0.104 mol) of pyridine. A clear solution formed on stirring. In a 20 mL sample bottle 2.33 g (3.2 eq of phosgene) of triphosgene was dissolved in 8 mL of methylene chloride and added to the reaction flask over 2 hours using the syringe pump. The reaction mixture was stirred for 15 minutes and then quenched with 250 mL of 9:1 mixture of THF-water. This was precipitated with 1500 mL of methanol in a beaker using overhead stirrer. Allowed to settle for 1 hour and then the supernatant was decanted off and discarded. The gluey precipitate at the bottom was washed with 200 mL of methanol with stirring. It was then washed with 200 mL of DI water. The residue was transferred to a PTFE dish and dried under vacuum for 24 hours at 50° C. The polymeric product became a gel during drying and hardened on cooling. DSC showed a melting point of 31.5° C.

Preparation Example 5

Polycaprolactone Diol (PCL-1300)

To a 250 mL round-bottomed flask were added 0.280 g (0.691 mmol) of Tin(II)2-ethylhexoate, 3.64 g (0.0478 mol) of 1,3-propane diol and 57.1 g (0.500 mol) of epsilon-caprolactone. The flask was purged with dry nitrogen and then maintained under a positive nitrogen pressure. The flask was then heated in an oil bath maintained at 150° C. for 8 hours (h) while stirring using a magnetic stirrer. It was then cooled to about 40° C. and dissolved in 120 mL of tetrahydrofuran (THF). Precipitation of the solution with 240 mL of hexane gave an oily product. The oily precipitate was stirred with fresh hexane until a white waxy solid was obtained. The end group analysis using by $^1$H NMR spectroscopy showed that the number average molecular weight (Mn) of the product was about 1300.

Using similar procedures and varying the molar ratios of 1,3-propane diol to that of epsilon-caprolactone, PCL-diols having molecular weights (Mn) of about 3000, about 5500, about 8400, about 10000, and about 20000 were prepared. PCL-diols may be referred to herein by the designation "PCL" followed by their approximate molecular weights, e.g., PCL-1250, PCL-3000, PCL-5500, PCL-8400, PCL-10000, PCL-20000, etc.

PCL diols having number average molecular weights (Mn) of about 1250 and about 10,000 were also prepared using 1,6-hexane diol as the initiator instead of 1,3-propane-diol.

Preparation Example 6

$I_2$DTE-PCL10k-PCL1.25k Polymer

Into a 1 L 4-necked round-bottomed flask equipped with a mechanical stirrer, a syringe pump, and a thermometer were added 20 g of 3,5-diiododesaminotyrosyl tyrosine ethyl ester ($I_2$DTE, 85 weight percent), 1.89 g (8 weight percent) of PCL-10000, and 1.65 g (7 weight percent) of PCL-1250. The PCL diols were prepared in the general manner described in Preparation Example 5. To the flask were then added 133 mL of methylene chloride and 26.5 mL of pyridine. On stirring a clear solution resulted to which a solution of 3.8 g of triphosgene in 12 mL of methylene chloride was added over a period of 2-3 hours using the syringe pump. After the addition was complete the reaction mixture was stirred for 15 min. The resulting viscous solution was stirred with 200 mL of water and the layers were allowed to separate. The top layer was separated and discarded. The bottom layer was precipitated with 220 mL of 2-propanol in a 1 L laboratory blender. The resulting oily precipitate was hardened by repeated grinding with 2-propanol in the blender. The $I_2$DTE-PCL10k-PCL1.25k polymer product obtained in the form of powder was dried in a vacuum oven at 40° C. to constant weight.

A number of other $I_2$DTE-PCL-PCL polymers were prepared using similar procedures by varying the molecular weight of the starting PCL diols by replacing the PCL-diol of Mn ~10,000 with PCL-diols of Mn=~3,000, ~5,500, ~8,400, ~20,000, and ~42,500. As indicated in Table 2, such $I_2$DTE-PCL-PCL polymers may be referred to herein by including the approximate molecular weights of the PCL diols in the "$I_2$DTE-PCL-PCL" designation. For example, the $I_2$DTE-PCL-PCL polymer made using $I_2$DTE, PCL-10000 and PCL-1250 may be referred to herein as $I_2$DTE-PCL10k-PCL1.25k.

Preparation Example 7

$I_2$DTE-PCL10k-PCL1.25k Polymer

An $I_2$DTE-PCL10k-PCL1.25k polymer was prepared as described in Preparation Example 6 using $I_2$DTE, PCL-10000, and PCL1250, except that the reaction mixture was filtered using a 40-60 micron fritted glass funnel. Precipitation of filtrate and further work up was carried out in a particle-controlled environment. The resulting $I_2$DTE-PCL10k-PCL1.25k polymer was found to show improved mechanical properties as compared to a corresponding polymer not prepared under particle-controlled conditions.

Preparation Example 8

$I_2$DTE-PHMC 12k

Into a 1 L 4-necked round-bottomed flask equipped with a mechanical stirrer, a syringe pump, and a thermometer were added 20 g of 3,5-diiododesaminitytyrosyl tyrosine ethyl ester ($I_2$DTE, 80 weight percent) and 5 g (20 weight percent) of poly(hexamethylene carbonate)-diol (Mn=12,000) (prepared in the manner similar to that described in Preparation Example 4). To the flask were then added 150 mL of methylene chloride and 10.3 mL of pyridine. On stirring a clear solution resulted to which a solution of 4.4 g of triphosgene in 17 mL of methylene chloride was added over a period of 2-3 hours using a syringe pump. After the addition was complete the reaction mixture was stirred for 15 min. The resulting viscous solution was quenched by adding a mixture of 15 mL of THF and 1.5 mL of water. After 15 min the quenched reaction mixture was precipitated with 250 mL of 2-propanol in a 1 L laboratory blender. The resulting oily precipitate was solidified by repeatedly grinding with 2-propanol in the blender. The product obtained in the form of powder was dried in a vacuum oven at 40° C. to constant weight. The resulting $I_2$DTE-PHMC12k polymer had a glass transition temperature of 125° C. As indicated by the aforementioned designation "$I_2$DTE-PHMC12k", polymers containing PHMC may be referred to herein in a manner similar to that described above for polymers containing PCL.

Preparation Example 9

DAT Macromer ("HDAT", DAT Diester of 1,6-Hexane Diol

Into a 500 mL round-bottomed flask equipped with an overhead stirrer, a Dean-Stark trap and a thermometer were added 11.8 g (0.10 mol) of 1,6-hexanediol, 33.6 g (0.202 mol) of DAT, 1.90 g (0.01 mol) of p-toluenesulfonic acid, and 200 mL of heptane. The flask was heated using a heating mantle, while stirring with the overhead stirrer. About 3.8 mL of water collected in the Dean-Stark trap and it did not increase further. The heating was stopped and the reaction mixture was allowed to cool to room temperature. The supernatant was removed by decantation and the residue in the flask was dried in a current of nitrogen. The off-white precipitate was dissolved in 100 mL of acetone and precipitated by repeated washing with 5% $NaHCO_3$ solution. The solid was then washed with deionized water (DI), isolated by filtration and dried. The product was further purified by extraction with diethyl ether (10 mL/g of solid) to provide the HDAT macromer product.

Preparation Example 10

Poly(HDAT Carbonate)-Diol Macromer

In a 1 L 4-necked flask with overhead stirrer were placed 9.5 g (22.8 mmol) of HDAT (prepared in the manner described in Preparation Example 9), 80 mL of methylene chloride and 6.8 g (86 mmol) of pyridine to the flask. A clear solution formed on stirring. In a 20 mL sample bottle 2.37 g of triphosgene (24.0 mmol of phosgene) was dissolved in 8 mL of methylene chloride and added to the reaction flask over 2 h using the syringe pump. The reaction mixture was stirred for 15 m and then quenched by stirring with 100 mL of water. This was precipitated with 135 mL of IPA in a beaker using overhead stirrer. The oily precipitate was triturated with several portions of IPA when the product was obtained as a solid. The residue was transferred to a PTFE dish and dried under vacuum for 24 h at 50° C. DSC of the resulting poly(HDAT carbonate)-diol macromer showed a Tg of 2.5° C., weight average molecular weight (Mw) about 38,000 and number average molecular weight (Mn) about 19,000 (Mw and Mn by GPC, polystyrene standards).

Preparation Example 11

$I_2$DTE-HDAT12k Polymer

Into a 1 L 4-necked round-bottomed flask equipped with a mechanical stirrer, a syringe pump, and a thermometer were added 20 g of 3,5-diiododesaminotyrosyl tyrosine ethyl ester (I$_2$DTE, 90 weight percent) and 2.22 g (10 weight percent) of poly(HDAT carbonate)-diol (Mn=19,000). To the flask were then added 180 mL of methylene chloride and 10.2 mL of pyridine. On stirring a clear solution resulted to which a solution of 3.8 g of triphosgene in 12 mL of methylene chloride was added over a period of 2-3 hours using a syringe pump. After the addition was complete the reaction mixture was stirred for 15 min. The resulting viscous solution was quenched by adding a mixture of 15 mL of THF and 1.5 mL of water. After 15 min the quenched reaction mixture was precipitated with 250 mL of 2-propanol in a 1 L laboratory blender. The resulting oily precipitate was solidified by repeatedly grinding with 2-propanol in the blender. The product obtained in the form of powder was dried in a vacuum oven at 40° C. to constant weight. The resulting I$_2$DTE-HDAT12k polymer had glass transition temperature of 129° C.

Preparation Example 12

I$_2$DTE-PCL10K Using Propane Diol as Plasticizer/Plastifier

Into a 1 L 4-necked round-bottomed flask equipped with a mechanical stirrer, a syringe pump, and a thermometer were added 20 g of 3,5-diiododesaminotyrosyl tyrosine ethyl ester (I$_2$DTE, 85 weight percent), 1.89 g (8 weight percent) of PCL10K and 1.65 g of propane diol (7 weight percent). To the flask were then added 133 mL of methylene chloride and 16.8 mL of pyridine. On stirring a clear solution resulted to which a solution of 5.9 g of triphosgene in 18 mL of methylene chloride was added over a period of 2-3 h using a syringe pump. After the addition was complete the reaction mixture was stirred for 15 min. The resulting viscous solution was quenched by adding a mixture of 15 mL of THF and 1.5 mL of water. After 15 min the quenched reaction mixture was precipitated with 250 mL of 2-propanol in a 1 L laboratory blender. The resulting oily precipitate was solidified by repeatedly grinding with 2-propanol in the blender. The product obtained in the form of powder was dried in a vacuum oven at 40° C. to constant weight. The resulting I$_2$DTE-PCL10K polymer had glass transition temperature of 98° C.

Test Examples 1-5

DMA Fatigue Testing of I$_2$DTE/PCL Copolymers

Fatigue testing of I$_2$DTE/PCL copolymers was conducted using DMA as follows: Polymer films with a thickness of 0.004±0.0002 inches were prepared by compression molding from dry polymer powder. Films were cut into rectangular strips 1 inch long and 0.2 inches wide and placed into 0.1 M PBS at pH 7.4 and at 37° C. for predetermined period of time (see Table 2). After soaking, the still wet samples were placed into the submersion film clamp of a DMA QO800 for fatigue testing. Fatigue testing was conducted in DMA Single Frequency Stress mode in which the submerged sample is held isothermally at a specified temperature and deformed (oscillated) at constant stress at a selected frequency. Tests were conducted until break of the test sample or until deformation of the sample reached full length of clamp separation allowed in submersion DMA clamp. Test samples were pre-loaded at minimum force before starting the test. The following DMA test parameters were used:

Pre-loading conditions: pre-load=0.01 N, force track 125%; initial amplitude=10 microns; soak time at 37° C.=variable (see Table 2).

Test conditions: isothermal temperature 37° C.; frequency=1.2 Hz; stress=10 MPa; Number of sweeps: up to 9999 (or until sample breaks or reaches max deformation allowed by DMA submersion clamp).

Table 2 shows the fatigue test results in terms of the time to break (in minutes) for samples aged in 0.1 M PBS at pH 7.4 and at 37° C. for one week, one month, and three months.

TABLE 2

| | | Time before break, minutes | | |
|---|---|---|---|---|
| No. | Polymer | Aging time 1 week | Aging time 1 month | Aging time 3 months |
| 1 | I$_2$DTE-PCL3k-PCL1.25k (85/8/7 w/w %) | 55 | 17 | <1 |
| 2 | I$_2$DTE-PCL5.5k-PCL1.25k (85/8/7 w/w %) | 77 | 22 | 2 |
| 4 | I$_2$DTE-PCL10k-PCL1.25k (85/8/7 w/w %) | 228 | 111 | 99 |
| 5 | I$_2$DTE-PCL42.5k-PCL1.25k (85/8/7 w/w %) | ≥300* (range 300-1200 min) | 293* | 43* |

The I$_2$DTE/PCL copolymers shown in Table 2 were prepared by copolymerizing I$_2$DTE ("I$_2$DTE"), a PCL macromer having a molecular weight of about 1250 ("PCL1.25k"), and various PCL macromers having molecular weights of from about 3,000 ("PCL3k") to about 42,500 ("PCL42.5k"). These copolymers contain an I$_2$DTE component having a wet Tg greater than 38° C. and a PCL component having a wet Tg of less than 36° C. The data in Table 2 illustrate the influence of PCL molecular weight on the toughness of the resulting polymer composition. The data in Table 2 shows that fatigue toughness (as indicated by resistance to failure in terms of time to break in DMA tests) increased as the molecular weight of the PCL increased from 3,000 to 5,500, with a particularly unexpected large increase in fatigue toughness as the PCL molecular weight increased to 10,000.

Test Examples 6-27

Stress at Yield (σ), Modulus (E), and Elongation at Break (∈) Data for Various Polymer Compositions The I$_2$DTE/PCL copolymers shown in Table 3 were tensile tested in the submerged state in water at 37° C. at a rate of deformation of 10 inches/min using an Instron 3343 equipped with submersion clamps. The I$_2$DTE-PTMO2.9k and I$_2$DTE-PTMO2.0k polymers were made in a manner similar to that described above for the I$_2$DTE-PCL and I$_2$DTE-PHMC polymers except that PTMO (polyteteramethylene oxide diol macromer) of the indicated molecular weight was used in place of PCL diol macromer or PHMC diol macromer, respectively Likewise, the I$_2$DTE-PCL10K-PEG2K polymer was made in a manner similar to that described above for the I$_2$DTE-PCL polymers except that PEG (polyethylene glycol diol macromer) of the indicated molecular weight was used in place of a portion of the PCL diol macromer. Prior to the testing, the samples were aged in PBS at 37° C. for predetermined periods of time (0, 1 week, and 3 months), as indicated in Table 3.

TABLE 3

| No. | Polymer Composition | Aging time 0 days | Aging time 1 week | Aging time 3 months |
|---|---|---|---|---|
| 6 | I$_2$DTE-PCL3k-PCL1.25k (85/8/7 w/w %) | σ = 7.6 ± 0.4 ksi<br>E = 226 ± 12 ksi<br>ε = 301 ± 105% | σ = 7.0 ± 0.3 ksi<br>E = 209 ± 11 ksi<br>ε = 33 ± 12% | σ = 5.9 ± 0.7 ksi<br>E = 213 ± 21 ksi<br>ε = 8 ± 3% |
| 7 | I$_2$DTE-PCL5.5k-PCL1.25k (85/8/7 w/w %) | σ = 7.9 ± 0.1 ksi<br>E = 216 ± 6 ksi<br>ε = 367 ± 43% | σ = 6.7 ± 0.2 ksi<br>E = 186 ± 6 ksi<br>ε = 32 ± 7% | σ = 6.4 ± 0.1 ksi<br>E = 206 ± 6 ksi<br>ε = 10 ± 5% |
| 8 | I$_2$DTE-PCL10k-PCL1.25k (85/8/7 w/w %) | σ = 7.4 ± 0.3 ksi<br>E = 193 ± 6 ksi<br>ε = 211 ± 108% | σ = 6.7 ± 0.1 ksi<br>E = 201 ± 10 ksi<br>ε = 96 ± 54% | σ = 6.5 ± 0.2 ksi<br>E = 180 ± 8 ksi<br>ε = 80 ± 55% |
| 9 | I$_2$DTE-PCL42.5k-PCL1.25k (85/8/7 w/w %) | σ = 7.5 ± 0.2 ksi<br>E = 209 ± 5 ksi<br>ε = 144 ± 113% | σ = 6.9 ± 0.3 ksi<br>E = 195 ± 8 ksi<br>ε = 196 ± 133% | σ = 6.7 ± 0.4 ksi<br>E = 200 ± 7 ksi<br>ε = 46 ± 13% |
| 10 | I$_2$DTE-PCL1.25k (89/11 w/w %) | σ = 9.1 ± 0.5 ksi<br>E = 251 ± 13 ksi<br>ε = 179 ± 125% | σ = 7.6 ± 0.34 ksi<br>E = 234 ± 11 ksi<br>ε = 32 ± 5% | σ = 7.6 ± 0.3 ksi<br>E = 267 ± 7 ksi<br>ε = 19 ± 7% |
| 11 | I2DTE-PCL10k (95/5 w/w %) | σ = 9.6 ± 0.5 ksi<br>E = 245 ± 10 ksi<br>ε = 54 ± 17% | σ = 8.21 ± 0.1 ksi<br>E = 230 ± 7 ksi<br>ε = 25 ± 4% | σ = 8.3 ± 0.4 ksi<br>E = 248 ± 12 ksi<br>ε = 20 ± 6% |
| 12 | I$_2$DTE-PCL10k (90/10 w/w %) | σ = 7.3 ± 0.3 ksi<br>E = 191 ± 12 ksi<br>ε = 220 ± 13% | σ = 6.7 ± 0.4 ksi<br>E = 195 ± 11 ksi<br>ε = 144 ± 15% | — |
| 13 | I$_2$DTE-PCL10k (85/15 w/w %) | σ = 6.7 ± 0.1 ksi<br>E = 171 ± 7 ksi<br>ε = 400 ± 50% | σ = 6.0 ± 0.4 ksi<br>E = 167 ± 7 ksi<br>ε = 248 ± 129% | σ = 6.3 ± 0.3 ksi<br>E = 183 ± 6 ksi<br>ε = 78 ± 65% |
| 14 | I$_2$DTE-PCL10k-PCL1.25k (85/9/6 w/w %) | σ = 7.0 ± 0.24 ksi<br>E = 191 ± 17 ksi<br>ε = 345 ± 115% | σ = 6.5 ± 0.2 ksi<br>E = 187 ± 8 ksi<br>ε = 163 ± 4 7% | σ = 7.0 ± 0.4 ksi<br>E = 210 ± 11 ksi<br>ε = 90 ± 82% |
| 15 | I$_2$DTE-PCL10k-PCL1.25k (86/7/7 w/w %) | σ = 6.9 ± 0.3 ksi<br>E = 190 ± 6 ksi<br>ε = 237 ± 123% | σ = 6.7 ± 0.1 ksi<br>E = 197 ± 6 ksi<br>ε = 43 ± 24% | σ = 6.9 ± 0.1 ksi<br>E = 211 ± 3 ksi<br>ε = 22 ± 7% |
| 16 | I$_2$DTE-PCL10k-PCL1.25k (90/7/3 w/w %) | σ = 8.2 ± 0.2 ksi<br>E = 232 ± 5 ksi<br>ε = 85 ± 31% | σ = 7.3 ± 0.2 ksi<br>E = 232 ± 9 ksi<br>ε = 29 ± 6% | 7.8 ± 0.2 ksi<br>E = 231 ± 5 ksi<br>ε = 23 ± 7% |
| 17 | I$_2$DTE-PCL10k-PCL1.25k (88/5/7 w/w %) | σ = 7.8 ± 0.2 ksi<br>E = 223 ± 6 ksi<br>ε = 150 ± 86% | σ = 7.2 ± 0.2 ksi<br>E = 231 ± 5 ksi<br>ε = 54 ± 22% | σ = 7.4 ± 0.1 ksi<br>E = 234 ± 1 ksi<br>ε = 26 ± 9% |
| 18 | I$_2$DTE-PCL10k-PCL1.25k (90/5/5 w/w %) | σ = 8.4 ± 0.4 ksi<br>E = 234 ± 10 ksi<br>ε = 138 ± 75% | σ = 7.8 ± 0.3 ksi<br>E = 235 ± 4 ksi<br>ε = 25 ± 5% | σ = 8.0 ± 0.2 ksi<br>E = 245 ± 4 ksi<br>ε = 32 ± 12% |
| 19 | I$_2$DTE-PHMC12K (95/5 w/w %) | σ = 9.4 ± 0.2 ksi<br>E = 225 ± 4 ksi<br>ε = 25 ± 4% | σ = 8.4 ± 0.15 ksi<br>E = 251 ± 10 ksi<br>ε = 19 ± 5% | σ = 8.9 ± 0.2 ksi<br>E = 263 ± 9 ksi<br>ε = 15 ± 6% |
| 20 | I$_2$DTE-PHMC12K (80/20 w/w %) | σ = 4.8 ± 0.9 ksi<br>E = 133 ± 8 ksi<br>ε = 420 ± 25% | σ = 4.7 ± 0.3 ksi<br>E = 150 ± 2 ksi<br>ε = 287 ± 30% | — |
| 21 | I$_2$DTE-PCL10k-PCL1.25k (79/10/11 w/w %) | σ = 4.3 ± 0.01 ksi<br>E = 143 ± 6 ksi<br>ε = 432 ± 67% | — | — |
| 22 | I$_2$DTE-PCL10K-PEG2K (85/8/7 w/w %) | σ = 6.9 ± 0.4 ksi<br>E = 201 ± 4 ksi<br>ε = 278 ± 179% | σ = 6.6 ± 0.4 ksi<br>E = 204 ± 10 ksi<br>ε = 149 ± 168% | σ = 6.5 ± 0.2 ksi<br>E = 210 ± 6 ksi<br>ε = 43 ± 33% |
| 23 | I$_2$DTE-PCL2k (80/20 w/w %) | σ = 5.7 ± 0.1 ksi<br>E = 161 ± 3 ksi<br>ε = 341 ± 26% | — | — |
| 24 | I$_2$DTE-PTMO2.9k (80/20 w/w %) | σ = 4.5 ± 0.2 ksi<br>E = 118 ± 6 ksi<br>ε >> 300% | — | — |
| 25 | I$_2$DTE-PTMO2.0k (70/30 w/w %) | σ = 1.9 ± 0.2 ksi<br>E = 46 ± 1 ksi<br>ε = 378 ± 17% | — | — |
| 26 | I$_2$DTE-PHMC12k-PCL1.25k (69/20/11 w/w %) | σ = 3.6 ± 0.1 ksi<br>E = 102 ± 2 ksi<br>ε >> 350% | — | — |
| 27 | I$_2$DTE (100%) | σ = 11.0 ± 0.5 ksi<br>E = 241 ± 7 ksi<br>ε = 9 ± 1% | — | — |

The data in Table 3 shows that values for elongation at break (∈) changes significantly during the aging of polymers, whereas stress at yield (σ) and elastic modulus (E) do not change as much. For polymers made from relatively lower molecular weight macromers, elongation at break drops to a greater extent during aging than for polymer made from relatively higher molecular weight macromers. For example, for polymer I₂DTE-PCL1.25k (89/11 w/w %), elongation at break decreased by about 5× after 1 week of aging, and for other polymers made from other relatively low molecular weight PCL macromers (I₂DTE-PCL3k-PCL1.25k (85/8/7 w/w %) and I₂DTE-PCL5.5k-PCL1.25k (85/8/7 w/w %)) elongation at break decreased by about 10× after aging for 1 week. On the other hand, for polymers made from PCL macromers having relatively higher molecular weights, elongation at break was maintained at relatively higher levels after the aging. For example, for polymer I₂DTE-PCL10k-PCL1.25k (85/8/7 w/w %), elongation at break was still 80% even after aging for 3 months.

Test Examples 28-39

Water content in polymers was determined by the Karl Fisher (KF) coulometric titration method using a commercially available KF Coulometric Titrator Aquastar AQC34. Thermo-pressed polymer films were submerged in 0.1M PBS at pH 7.4 at 37° C. and soaked for 24 hours to reach equilibrium water content, then blotted to remove excess water from the surface prior to determination of water content by the Karl Fisher method. Water content results (weight percent based on total) for various polymers are shown in Table 4.

TABLE 4

| No. | Polymer | Water content, % |
|---|---|---|
| 28 | I₂DTE-PCL10k (85/15 w/w %) | 1.3 |
| 29 | I₂DTE-PCL10k (90/10 w/w %) | 1.4 |
| 30 | I₂DTE-PCL10k (95/5 w/w %) | 1.6 |
| 31 | I₂DTE-PCL1.25k (89/11 w/w %) | 1.4 |
| 32 | I₂DTE-PCL3k-PCL1.25k (85/8/7 w/w %) | 1.2 |
| 33 | I₂DTE-PCL5.5k-PCL1.25k (85/8/7 w/w %) | 1.4 |
| 34 | I₂DTE-PCL10k-PCL1.25k (85/8/7 w/w %) | 1.2 |
| 35 | I₂DTE-PCL42.5k-PCL1.25k (85/8/7 w/w %) | 1.3 |
| 36 | I₂DTE-PCL10k-PCL1.25k (90/5/5 w/w %) | 1.3 |
| 37 | I₂DTE-PCL10k-PCL1.25k (86/7/7 w/w %) | 1.2 |
| 38 | I₂DTE-PCL10k-PCL1.25k (86/9/6 w/w %) | 1.1 |
| 39 | I₂DTE-PHMC12k (95/5 w/w %) | 1.5 |

The data shown in Table 4 show a slight trend of decreasing equilibrium water content as the PCL content increases.

The following examples demonstrate the conversion of monomer and polymers with amide groups to monomer and polymers with acyl-imino groups.

Example 40

Preparation of Acyl-Imine-Containing Polycarbonates by Reacting Monomer with Excess Triphosgene In a 500 mL round bottomed flask were placed 15 g (0.042 mol) of desaminotyrosyl tyrosine ethyl ester (DTE) 0.011 g (0.07 mmol) of ethyl 4-hydroxybenzoate (endcapping agent), 12.45 g (0.16 mol) of pyridine, and 150 mL of methylene chloride and stirred under a nitrogen atmosphere. Triphosgene (6.65 g, 0.067 mol of phosgene) was dissolved in 37 mL of methylene chloride and the solution was added to the flask using a syringe pump over a 2 h period. After the addition was complete the reaction mixture was stirred for 17 h. The reaction mixture was precipitated with 1 L of 2-propanol in a 4 L blender. The resulting gel like product was ground repeatedly with 0.5 L of 2-propanol. The solid product was isolated by filtration and ground with Deionized water and finally dried in a vacuum oven. ¹H NMR indicated a ratio of 2:1 of imine (—C=N—) to amide (—CH—NH—).

Example 41

Preparation of an Acyl-Imine-Containing Polycarbonate

In a 250 mL round bottomed flask were placed 10 g of poly(DTE carbonate) (PDTEC; 0.026 mol repeat units), pyridine (2.57 g, 0.026 mol), and 100 mL of methylene chloride. To the resulting solution was added with stirring a solution of triphosgene (1.29 g, 0.013 mol of phosgene) in 5 mL of methylene chloride over a 90 min period. The reaction mixture was stirred at ambient temperature for 24 h and then precipitated with 500 mL of 2-propanol in a blender. The resulting yellow polymer was washed twice with 250 mL portions of 2-propanol, isolated by filtration and dried in vacuum oven at 40° C. The polymer was characterized by ¹H NMR, and gel permeation chromatography. ¹H NMR indicated that 30% of the —CH—NH— groups had been converted to —C=N— groups.

It will be understood by those of skill in the art that numerous and various modifications can be made without departing from the spirit of the present invention. Therefore, it should be clearly understood that the various embodiments of the present invention described herein are illustrative only and not intended to limit the scope of the present invention.

What is claimed is:

1. A biocompatible polymer composition, comprising at least a first polymer phase and a second polymer phase;

the first polymer phase having at least one first wet thermal transition temperature selected from a first wet glass transition temperature and a first wet melting point, the first wet thermal transition temperature being at least 38° C.;

the first polymer phase comprising a number (n) of first recurring units of the formula (I):

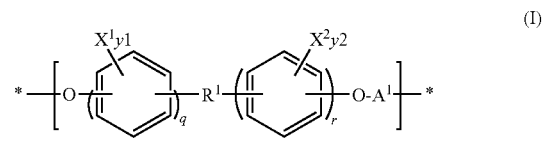

wherein:

$X^1$ and $X^2$ are each independently selected from the group consisting of halogen, halomethyl, halomethoxy, methyl, methoxy, thiomethyl, nitro, sulfoxide, and sulfonyl; $y^1$ and $y^2$ indicate the number of $X^1$ and $X^2$ groups, respectively, and are each independently zero or an integer in the range of 1 to 4;

q and r are each independently zero or one, where q+r=1 or 2;

each $A^1$ is independently selected from the group consisting of

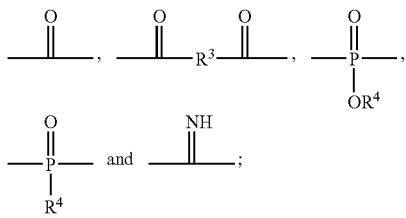

each $R^3$ is independently selected from the group consisting of $C_1$-$C_{30}$ alkyl, $C_1$-$C_{30}$ heteroalkyl, $C_5$-$C_{30}$ aryl, $C_6$-$C_{30}$ alkylaryl, and $C_2$-$C_{30}$ heteroaryl;

each $R^4$ independently selected from the group consisting of H, $C_1$-$C_{30}$ alkyl, and $C_1$-$C_{30}$ heteroalkyl;

each $R^1$ is independently selected from the group consisting of

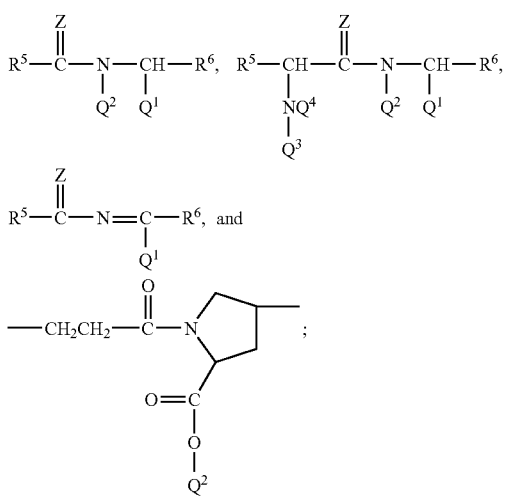

provided that when $R^1$ is

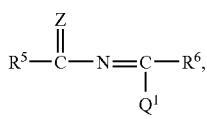

$Q_1$ is $COOR_4$ and when $R^1$ is

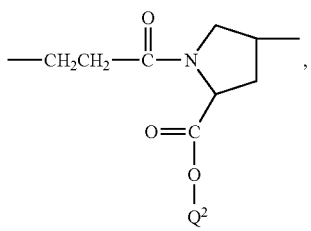

r=0;

$R^5$ is selected from the group consisting of —CH=CH—, —CHJ$^1$-CHJ$^2$-, —(CH$_2$)$_a$—, optionally ring-halogenated

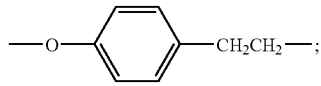

and optionally ring-halogenated

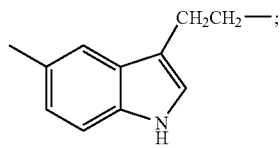

wherein q=0 when $R^5$ is

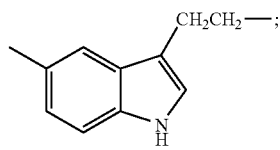

$R^6$ is selected from the group consisting of —CH=CH—, —CHJ$^1$-CHJ$^2$-, —(CH$_2$)$_a$—, optionally ring-halogenated

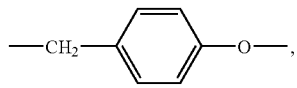

and optionally ring-halogenated

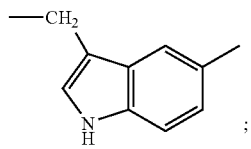

wherein r=0 when $R^6$ is;

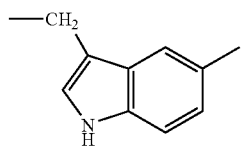

each a is independently zero or an integer in the range of 1 to 8;

$J^1$ and $J^2$ are each independently selected from the group consisting of Br and I;

each Z is independently an O or an S; and $Q^1$ and $Q^4$ are each independently H, CH$_2$—R$^4$, COOR$^4$ or a crystallizable group comprising from about 6 to about 30 carbon atoms;

$Q^2$ and $Q^3$ are each independently H, $CH_2$—$R^4$, or a crystallizable group comprising from about 6 to about 30 carbon atoms;

the second polymer phase having at least one second wet thermal transition temperature selected from a second wet glass transition temperature and a second wet melting point, the second wet thermal transition temperature being 36° C. or lower, the second polymer phase comprising a number (m) of second recurring units of the formula (IId):

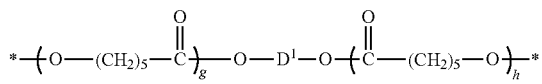

(IId)

wherein $D^1$ is $C_1$-$C_{24}$ alkylene and g and h are selected so that the formula (IId) structure has a molecular weight in the range of about 2,000 to about 40,000;

wherein the number (n) and the number (m) are selected to control the relative amounts of the first polymer phase and the second polymer phase so that (a) the polymer composition is phase-separated over at least the temperature range of about 25° C. to about 50° C., (b) the polymer composition has a water content of 4.5% or less as measured after soaking for 24 hours at 37° C. in 0.1 M phosphate buffered saline (PBS) at pH 7.4; and (c) the volume fraction of the second polymer phase in the polymer composition is in the range of about 6% to about 40%, based on total volume.

2. The polymer composition of claim 1, wherein the volume fraction of the second polymer phase in the polymer composition is in the range of about 7% to about 33%, based on total volume.

3. The polymer composition of claim 1, wherein the volume fraction of the second polymer phase in the polymer composition is in the range of about 7% to about 26%, based on total volume.

4. The polymer composition of claim 1, wherein the volume fraction of the second polymer phase in the polymer composition is in the range of about 7% to about 20%, based on total volume.

5. The polymer composition of claim 1, wherein the volume fraction of the second polymer phase in the polymer composition is in the range of about 7% to about 16%, based on total volume.

6. The polymer composition of claim 1, wherein the volume fraction of the second polymer phase in the polymer composition is in the range of about 9% to about 16%, based on total volume.

7. The polymer composition of claim 1, wherein the volume fraction of the second polymer phase in the polymer composition is in the range of about 9% to about 13%, based on total volume.

8. The polymer composition of claim 1, wherein the volume fraction of the second polymer phase in the polymer composition is in the range of about 10% to about 13%, based on total volume.

9. The polymer composition of claim 1, wherein the volume fraction of the second polymer phase in the polymer composition is in the range of about 10% to about 12%, based on total volume.

10. The polymer composition of claim 1, wherein the polymer composition has a water content of 3% or less as measured after soaking for 24 hours at 37° C. in 0.1 M phosphate buffered saline (PBS) at pH 7.4.

11. The polymer composition of claim 1, wherein the number (n) and the number (m) are further selected to control the ductility properties of the polymer composition, such that the polymer composition has an elongation at break of greater than 30%, a Young's modulus of greater than 130 ksi and a strength at yield of greater than 4.0 ksi, when tested under tensile test conditions that comprise (i) providing a tensile test strip having measurements of 0.2 inches wide, a gauge length of 1.0 inches and a thickness of 0.004 inches, (ii) aging the tensile test strip for 7 days at 37° C. in 0.1 M phosphate buffered saline (PBS) at pH 7.4, and (iii) pulling the aged tensile test strip at a rate of 10 inches per minute while submerged in water at 37° C.

12. The polymer composition of claim 11, wherein the polymer composition has an elongation at break of greater than 50%.

13. The polymer composition of claim 11, wherein the polymer composition has an elongation at break of greater than 70%.

14. The polymer composition of claim 13, wherein the polymer composition has a Young's modulus of greater than 180 ksi and a strength at yield of greater than 6.4 ksi.

15. The polymer composition of claim 1, wherein the number (n) and the number (m) are further selected to control the fatigue properties of the polymer composition, such that the polymer composition remains intact for at least 60 minutes when tested under fatigue test conditions that comprise (i) providing a fatigue test strip having measurements of 5.0 mm wide, a gauge length of 15 mm and a thickness of 0.1 mm, (ii) aging the fatigue test strip for 7 days at 37° C. in 0.1 M phosphate buffered saline (PBS) at pH 7.4, and (iii) subjecting the aged fatigue test strip to oscillating deformation at a frequency of 1.2 Hz under a stress of 10 MPa in single frequency stress mode while submerged in water at 37° C.

16. The polymer composition of claim 15, wherein the polymer composition remains intact for at least 80 minutes.

17. The polymer composition of claim 15, wherein the polymer composition remains intact for at least 100 minutes.

18. The polymer composition of claim 1, wherein the polymer composition comprises a block copolymer, the block copolymer comprising at least one block of said first recurring units and at least one block of said second recurring units, wherein the block copolymer is phase-separated so that more than about half of the first block is in the first polymer phase and more than about half of the second block is in the second polymer phase.

19. The polymer composition of claim 1, further comprising third recurring units having a formula selected from the group consisting of the formula (IIa), the formula (IIb), the formula (IIc), and the formula (IIe):

(IIa)

(IIb)

(IIc)

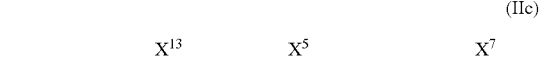

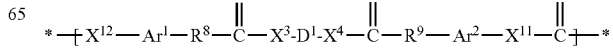

-continued $$* -\!\!\left[\!X^{12}\!-\!R^8\!-\!\overset{X^{13}}{\overset{\|}{C}}\right]_{\!g}\!\!X^3\text{-}D^1\text{-}X^4\!-\!\!\left(\!\overset{X^5}{\overset{\|}{C}}\!-\!R^9\!-\!X^{11}\right)_{\!h}\!\!\overset{X^7}{\overset{\|}{C}}\!-\!\! \quad \text{(IId)}$$

wherein $X^3$, $X^4$, $X^5$, $X^7$, $X^8$, $X^9$, $X^{10}$, $X^{11}$, $X^{12}$ and $X^{13}$ are each independently selected from the group consisting of O, S and $NR^{10}$, where $R^{10}$ is selected from hydrogen and an alkyl group containing from one to 30 carbon atoms;

- $Ar^1$ and $Ar^2$ are phenyl rings optionally substituted with from one to four substituents independently selected from the group consisting of a halogen, a halomethyl, a halomethoxy, a methyl, a methoxy, a thiomethyl, a nitro, a sulfoxide, and a sulfonyl;
- $R^8$ and $R^9$ contain from one to ten carbon atoms each and are independently selected from the group consisting of an optionally substituted alkylene, an optionally substituted heteroalkylene, an optionally substituted alkenylene, and an optionally substituted heteroalkenylene;
- g and h in formula (IIe) are each independently integers in the range of about 1 to about 500; and
- D and $D^2$ contain up to 24 carbon atoms and are independently selected from the group consisting of an optionally substituted alkylene, an optionally substituted heteroalkylene, an optionally substituted alkenylene and an optionally substituted heteroalkenylene;
- and when said third recurring units have a structure represented by the formula (IId), the variables g and h for said second recurring units differ from the variables g and h for said third recurring units.

20. The polymer composition of claim 19, wherein for the formula (IIe), $X^3$, $X^4$, $X^5$, $X^7$, $X^{11}$, $X^{12}$, and $X^{13}$ are all O; $R^8$ and $R^9$ are both $-(CH_2)_5-$, and $D^1$ is $C_1$-$C_{24}$ alkylene.

21. The polymer composition of claim 1, wherein q=r=1; $X^1$ is I; $y^1$=2; $X^2$ is H;

$R^1$ is $$R^5-\overset{Z}{\overset{\|}{C}}-\underset{Q^2}{\overset{}{N}}-\underset{Q^1}{\overset{}{CH}}-R^6;$$

$A^1$ is $$-\!\!\overset{O}{\overset{\|}{\rule{1em}{0.4pt}}}\!\!-;$$

$R^5$ is $-(CH_2CH_2)-$; Z is O; $Q^2$ is H; $Q^1$ is $-COOCH_2CH_3$; $R^6$ is $-CH_2-$; and g and h for the second recurring units of the formula (IId) are each independently integers such that the sum of g +h is in the range of about 10 to about 15.

22. The polymer composition of claim 1, wherein q=1; r=1; $X^1$ is I; $y^1$=2; $X^2$ is H;

$R^1$ is $$R^5-\overset{Z}{\overset{\|}{C}}-\underset{Q^2}{\overset{}{N}}-\underset{Q^1}{\overset{}{CH}}-R^6;$$

$A^1$ is $$-\!\!\overset{O}{\overset{\|}{\rule{1em}{0.4pt}}}\!\!-;$$

$R^5$ is $-(CH_2CH_2)-$; Z is O; $Q^2$ is H; $Q^1$ is $-COOCH_2CH_3$; $R^6$ is $-CH_2-$; and g and h for the second recurring units of the formula (IId) are each independently integers such that the sum of g +h is in the range of about 18 to about 26.

23. The polymer composition of claim 1, wherein q=1; r=1; $X^1$ is I; $y^1$=2; $X^2$ is H;

$R^1$ is $$R^5-\overset{Z}{\overset{\|}{C}}-\underset{Q^2}{\overset{}{N}}-\underset{Q^1}{\overset{}{CH}}-R^6;$$

$A^1$ is $$-\!\!\overset{O}{\overset{\|}{\rule{1em}{0.4pt}}}\!\!-;$$

$R^5$ is $-(CH_2CH_2)-$; Z is O; $Q^2$ is H; $Q^1$ is $-COOCH_2CH_3$; $R^6$ is $-CH_2-$; and g and h for the second recurring units of the formula (IId) are each independently integers such that the sum of g +h is in the range of about 32 to about 39.

24. The polymer composition of claim 1, wherein q=1; r=1; $X^1$ is I; $y^1$=2; $X^2$ is H;

$R^1$ is $$R^5-\overset{Z}{\overset{\|}{C}}-\underset{Q^2}{\overset{}{N}}-\underset{Q^1}{\overset{}{CH}}-R^6;$$

$A^1$ is $$-\!\!\overset{O}{\overset{\|}{\rule{1em}{0.4pt}}}\!\!-;$$

$R^5$ is $-(CH_2CH_2)-$; Z is O; $Q^2$ is H; $Q^1$ is $-COOCH_2CH_3$; $R^6$ is $-CH_2-$; and g and h for the second recurring units of the formula (IId) are each independently integers such that the sum of g +h is in the range of about 36 to about 52.

25. The polymer composition of claim 1, wherein q=1; r=1; $X^1$ is I; $y^1$=2; $X^2$ is H;

R¹ is

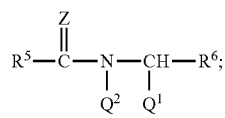

A¹ is

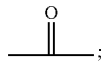

$R^5$ is —(CH₂CH₂)—; Z is O; $Q^2$ is H; $Q^1$ is —COOCH₂CH₃; $R^6$ is —CH₂—; and g and h for the second recurring units of the formula (IId) are each independently integers such that the sum of g +h is in the range of about 79 to about 96.

26. The polymer composition of claim 1, wherein q=1; r=1; $X^1$ is I; $y^1$=2; $X^2$ is H;

R¹ is

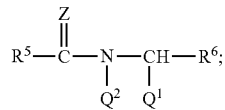

$A^l$ is

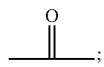

$R^5$ is —(CH₂CH₂)—; Z is O; $Q^2$ is H; $Q^1$ is —COOCH₂CH₃; $R^6$ is —CH₂—; and g and h for the second recurring units of the formula (IId) are each independently integers such that the sum of g +h is in the range of about 170 to about 200.

27. The polymer composition of claim 1, wherein the weight fraction of the second polymer phase in the polymer composition is in the range of about 6% to about 20%, based on total weight.

28. The polymer composition of claim 1, wherein the weight fraction of the second polymer phase in the polymer composition is in the range of about 8% to about 18%, based on total weight.

29. The polymer composition of claim 1, wherein the weight fraction of the second polymer phase in the polymer composition is in the range of about 10% to about 15%, based on total weight.

30. The polymer composition of claim 1 that is bioresorbable, biodegradable, or both.

31. The polymer composition of claim 1, wherein the first recurring units of the formula (I) are selected to contain sufficient halogen atoms to render the polymer composition inherently radiopaque.

32. The polymer composition of claim 1, wherein q=1; r=1; R¹ is independently selected from the group consisting of

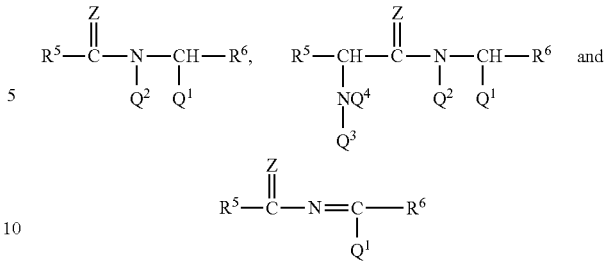

wherein $Q^1$ is COOR⁴; and $Q^2$, $Q^3$, and $Q^4$ are all hydrogen.

33. The polymer composition of claim 1, wherein A¹ is

34. The polymer composition of claim 1, wherein q=0.
35. The polymer composition of claim 1, wherein r=0.
36. The polymer composition of claim 1, further comprising a radiopacifying agent in an amount effective to render the polymer composition radiopaque.
37. The polymer composition of claim 1, further comprising a biologically active compound.
38. The polymer composition of claim 37, wherein the biologically active compound is covalently attached to the first polymer phase, the second polymer phase or both.
39. The polymer composition of claim 1, wherein the first polymer phase is at least partially crystalline at a temperature below 37° C.
40. The polymer composition of claim 39, wherein the first recurring units of the formula (I) are selected such that the first polymer phase contains sufficient crystallizable side chains to render the first polymer phase at least partially crystalline at a temperature below 37° C.
41. A medical device comprising the polymer composition of claim 1.
42. The medical device of claim 41, wherein the polymer composition further comprising a biologically active compound.
43. The medical device of claim 42, wherein the bioactive agent is selected from the group consisting of a chemotherapeutic agent, a non-steroidal anti-inflammatory, a steroidal anti-inflammatory, and a wound healing agent.
44. The medical device of claim 41, wherein the medical device is a stent.
45. The medical device of claim 44, wherein the number (n) and the number (m) are further selected to control the fatigue properties of the polymer composition, such that the polymer composition remains intact for at least 60 minutes when tested under fatigue test conditions that comprise (i) providing a fatigue test strip having measurements of 5.0 mm wide, a gauge length of 15 mm and a thickness of 0.1 mm, (ii) aging the fatigue test strip for 7 days at 37° C. in 0.1 M phosphate buffered saline (PBS) at pH 7.4, and (iii) subjecting the aged fatigue test strip to oscillating deformation at a frequency of 1.2 Hz under a stress of 10 MPa in single frequency stress mode while submerged in water at 37° C.
46. A medical device comprising the polymer composition of claim 21.
47. The medical device of claim 46, wherein the volume fraction of the second polymer phase in the polymer composition is in the range of about 7% to about 33%, based on total volume.

48. The medical device of claim 46, wherein the medical device is a stent.

49. The medical device of claim 48, wherein the number (n) and the number (m) are further selected to control the fatigue properties of the polymer composition, such that the polymer composition remains intact for at least 60 minutes when tested under fatigue test conditions that comprise (i) providing a fatigue test strip having measurements of 5.0 mm wide, a gauge length of 15 mm and a thickness of 0.1 mm, (ii) aging the fatigue test strip for 7 days at 37° C. in 0.1 M phosphate buffered saline (PBS) at pH 7.4, and (iii) subjecting the aged fatigue test strip to oscillating deformation at a frequency of 1.2 Hz under a stress of 10 MPa in single frequency stress mode while submerged in water at 37° C.

50. A method of treating a body lumen, comprising deploying the stent of claim 44 within the body lumen.

51. A method of treating a body lumen, comprising deploying the stent of claim 48 within the body lumen.

52. A medical device comprising the polymer composition of claim 24.

53. The medical device of claim 52, wherein the volume fraction of the second polymer phase in the polymer composition is in the range of about 7% to about 33%, based on total volume.

54. The medical device of claim 52, wherein the medical device is a stent.

55. The medical device of claim 54, wherein the number (n) and the number (m) are further selected to control the fatigue properties of the polymer composition, such that the polymer composition remains intact for at least 60 minutes when tested under fatigue test conditions that comprise (i) providing a fatigue test strip having measurements of 5.0 mm wide, a gauge length of 15 mm and a thickness of 0.1 mm, (ii) aging the fatigue test strip for 7 days at 37° C. in 0.1 M phosphate buffered saline (PBS) at pH 7.4, and (iii) subjecting the aged fatigue test strip to oscillating deformation at a frequency of 1.2 Hz under a stress of 10 MPa in single frequency stress mode while submerged in water at 37° C.

56. A biocompatible polymer composition, comprising:
a number (n) of first polymer recurring units of formula (I):

$$*-\left[-O-\left(\!\!\bigcirc\!\!\right)_q^{X^1_{y1}}-R^1-\left(\!\!\bigcirc\!\!\right)_r^{X^2_{y2}}-O-A^1-\right]-*\quad (I)$$

wherein:
$X^1$ and $X^2$ are each independently selected from the group consisting of halogen, halomethyl, halomethoxy, methyl, methoxy, thiomethyl, nitro, sulfoxide, and sulfonyl; $y^1$ and $y^2$ indicate the number of $X^1$ and $X^2$ groups, respectively, and are each independently zero or an integer in the range of 1 to 4;

q and r are each independently zero or one, where q+r=1 or 2;

each $A^1$ is independently selected from the group consisting of and each $R^3$ is independently selected from the group consisting of $C_1$-$C_{30}$ alkyl, $C_1$-$C_{30}$ heteroalkyl, $C_5$-$C_{30}$ aryl, $C_6$-$C_{30}$ alkylaryl, and $C_2$-$C_{30}$ heteroaryl;

each $R^4$ independently selected from the group consisting of H, $C_1$-$C_{30}$ alkyl, $C_1$-$C_{30}$ heteroalkyl, each $R^1$ is independently selected from the group consisting of provided that when $R^1$ is $Q_1$ is $COOR_4$ and when $R^1$ is r=0;

$R^5$ is selected from the group consisting of —CH=CH—, —CHJ$^1$-CHJ$^2$-, —(CH$_2$)$_a$—, optionally ring-halogenated

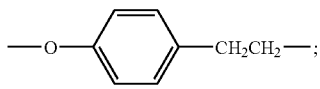

and optionally ring-halogenated

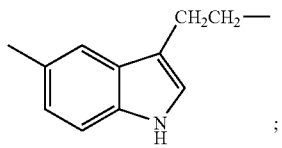

wherein q=0 when $R^5$ is

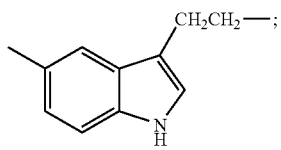

$R^6$ is selected from the group consisting of —CH=CH—, —CHJ$^1$-CHJ$^2$-, —(CH$_2$)$_a$—, optionally ring-halogenated

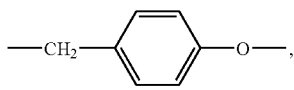

and optionally ring-halogenated

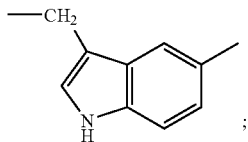

wherein r=0 when $R^6$ is

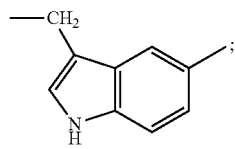

each a is independently zero or an integer in the range of 1 to 8;

J$^1$ and J$^2$ are each independently selected from the group consisting of Br and I; each Z is independently an O or an S; and $Q^1$ and $Q^4$ are each independently H, CH$_2$—R$^4$, COOR$^4$ or a crystallizable group comprising from about 6 to about 30 carbon atoms;

$Q^2$ and $Q^3$ are each independently H, CH$_2$—R$^4$, or a crystallizable group comprising from about 6 to about 30 carbon atoms; and a number (m) of second polymer recurring units of the formula (IId):

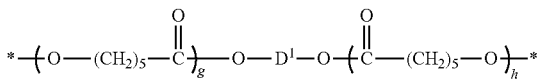

(IId)

wherein D$^1$ is C$_1$-C$_{24}$ alkylene and g and h are selected so that the formula (IId) structure has a molecular weight in the range of about 2,000 to about 40,000; and the number (m) of second polymer recurring units is effective to result in phase separation of said polymer composition into first and second polymer phases, wherein said second phase comprises said second polymer recurring units;

wherein the polymer composition has a water content of 4.5% or less as measured after soaking for 24 hours at 37° C. in 0.1 M phosphate buffered saline (PBS) at pH 7.4; and the second polymer recurring units and the number values for (n) and (m) are selected so that said polymer composition remains intact for at least about 15 minutes when tested under fatigue test conditions that comprise (i) providing a fatigue test strip having measurements of 5.0 mm wide, a gauge length of 15 mm and a thickness of 0.1 mm, (ii) aging the fatigue test strip for 7 days at 37° C. in 0.1 M phosphate buffered saline (PBS) at pH 7.4, and (iii) subjecting the aged fatigue test strip to oscillating deformation at a frequency of 1.2 Hz under a stress of 10 MPa in single frequency stress mode while submerged in water at 37° C.

57. The polymer composition of claim 56, further comprising third polymer recurring units selected from the group consisting of linear C$_1$-C$_{30}$ poly(alkylene diol), and branched C$_1$-C$_{30}$ poly(alkylene oxide).

58. The polymer composition of claim 46, wherein more than about half of the second polymer recurring units are in the second polymer phase.

59. The polymer composition of claim 56, wherein the polymer composition comprises a block copolymer, the block copolymer comprising at least one block of said first recurring units and at least one block of said second recurring units, and the block copolymer is phase-separated so that said second phase comprises more than about half of the second recurring units of said polymer composition.

60. The polymer composition of claim 59, wherein the polymer of said composition comprises a random block copolymer comprising at least one block of said first recurring unit and at least one block of said second recurring unit.

61. The polymer composition of claim 56, wherein the polymer of said composition consists of a random block copolymer comprising at least one block of said first recurring unit and at least one block of said second recurring unit.

* * * * *